(12) United States Patent
Lattouf

(10) Patent No.: US 11,737,769 B2
(45) Date of Patent: Aug. 29, 2023

(54) CLOT RETRIEVERS AND METHODS FOR DEPLOYMENT

(71) Applicant: Omar M. Lattouf, Atlanta, GA (US)

(72) Inventor: Omar M. Lattouf, Atlanta, GA (US)

( * ) Notice: Subject to any disclaimer, the term of this patent is extended or adjusted under 35 U.S.C. 154(b) by 518 days.

(21) Appl. No.: 16/410,912

(22) Filed: May 13, 2019

(65) Prior Publication Data

US 2020/0029983 A1 Jan. 30, 2020

Related U.S. Application Data

(63) Continuation-in-part of application No. PCT/US2017/066789, filed on Dec. 15, 2017.

(60) Provisional application No. 62/672,383, filed on May 16, 2018, provisional application No. 62/436,920, filed on Dec. 20, 2016.

(51) Int. Cl.
*A61B 17/221* (2006.01)
*A61B 17/00* (2006.01)
*A61B 17/22* (2006.01)

(52) U.S. Cl.
CPC .... *A61B 17/221* (2013.01); *A61B 2017/0042* (2013.01); *A61B 2017/00287* (2013.01); *A61B 2017/00867* (2013.01); *A61B 2017/22072* (2013.01)

(58) Field of Classification Search
CPC .......... A61B 2017/00287; A61B 2017/00292; A61B 2017/2212; A61B 17/221; A61B 2017/0042; A61B 2017/22072; A61B 2017/00991; A61B 5/6858; A61B 17/32056; A61B 2017/00867
USPC ................. 606/127, 110, 113, 114, 200, 151
See application file for complete search history.

(56) References Cited

U.S. PATENT DOCUMENTS

| | | | |
|---|---|---|---|
| 5,037,379 A * | 8/1991 | Clayman | A61B 17/00234 600/37 |
| 6,001,118 A | 12/1999 | Daniel et al. | |
| 6,245,087 B1 * | 6/2001 | Addis | A61B 17/221 606/200 |
| 7,695,491 B2 | 4/2010 | Clubb | |
| 9,351,749 B2 | 5/2016 | Brady et al. | |
| 9,402,708 B2 | 8/2016 | Holloway | |
| 2002/0095171 A1* | 7/2002 | Belef | 606/200 |
| 2003/0100919 A1 | 5/2003 | Hopkins et al. | |
| 2003/0176884 A1 | 9/2003 | Berrada et al. | |
| 2004/0153119 A1 | 8/2004 | Kusleika et al. | |

(Continued)

FOREIGN PATENT DOCUMENTS

WO WO-2011110356 A1 9/2011
WO WO-2018118706 A1 6/2018

OTHER PUBLICATIONS

Funnel Definition and Meaning, Collins English Dictionary, accessed Sep. 23, 22, Copyright Collins 2022 (Year: 2022).*

(Continued)

*Primary Examiner* — Kankindi Rwego
(74) *Attorney, Agent, or Firm* — Wilson Sonsini Goodrich & Rosati

(57) ABSTRACT

Methods and devices for catheter-based removal of unwanted tissue or occlusive matter from blood vessels and other body lumens rely on a wire advanced from a tube to deploy a capture net that can be drawn over the clot. Apparatus include simple and reliable mechanisms for deployment of nets, funnels, and other clot capturing mechanisms for retrieving clot material from inside a blood vessel.

6 Claims, 23 Drawing Sheets

(56) References Cited

U.S. PATENT DOCUMENTS

| | | |
|---|---|---|
| 2005/0055047 A1 | 3/2005 | Greenhalgh |
| 2009/0240238 A1 | 9/2009 | Grodrian et al. |
| 2010/0042107 A1* | 2/2010 | Merrifield ............ A61B 17/221 |
| | | 606/106 |
| 2011/0125181 A1 | 5/2011 | Brady et al. |
| 2011/0184435 A1* | 7/2011 | Parihar ............ A61B 17/00234 |
| | | 606/114 |
| 2011/0230909 A1 | 9/2011 | Kucharczyk et al. |
| 2013/0184739 A1* | 7/2013 | Brady .................. A61B 17/221 |
| | | 606/200 |
| 2013/0197567 A1 | 8/2013 | Brady et al. |
| 2013/0310803 A1* | 11/2013 | Morsi .............. A61B 17/22032 |
| | | 604/508 |
| 2014/0276922 A1 | 9/2014 | McLain et al. |
| 2016/0143722 A1 | 5/2016 | Steinmetz |
| 2016/0192956 A1 | 7/2016 | Brady et al. |
| 2016/0220346 A1 | 8/2016 | Bonnette et al. |

OTHER PUBLICATIONS

Tandem Definition and Meaning, Merriam-Webster, accessed Sep. 23, 2022, Copyright Merriam-Webster, Incorporated 2022 (Year: 2022).*

* cited by examiner

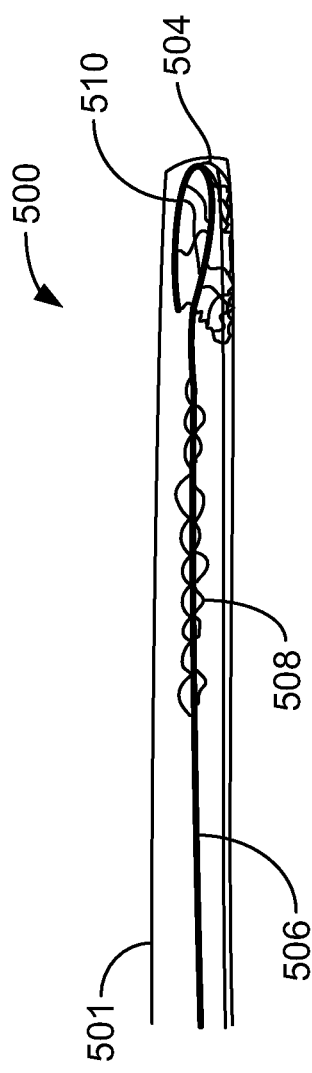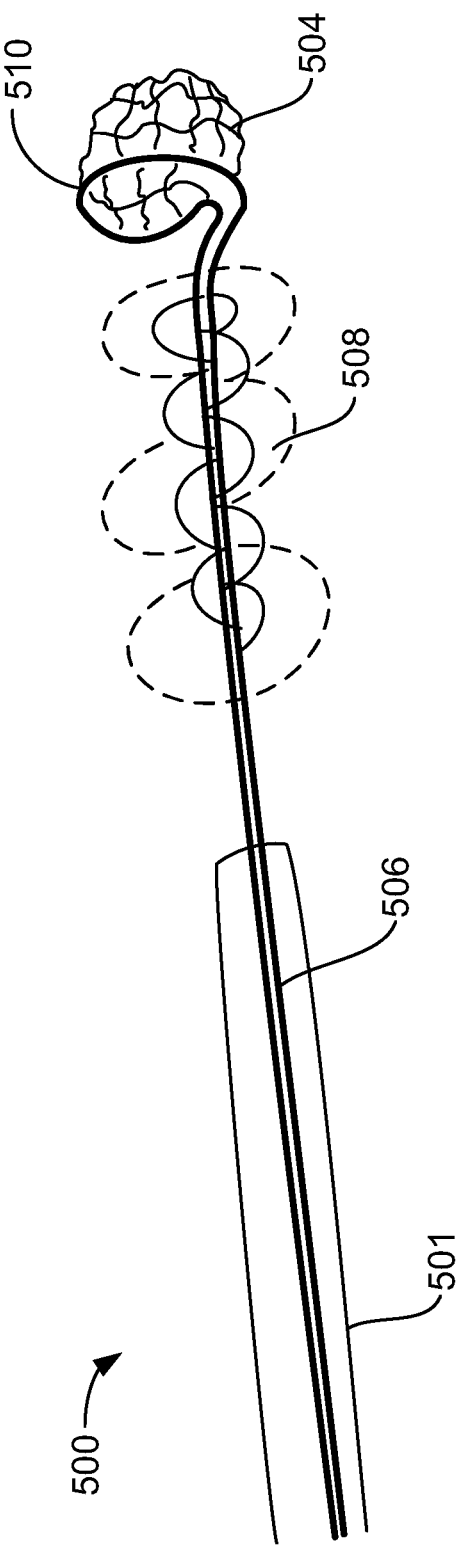
FIG. 13A
FIG. 13B

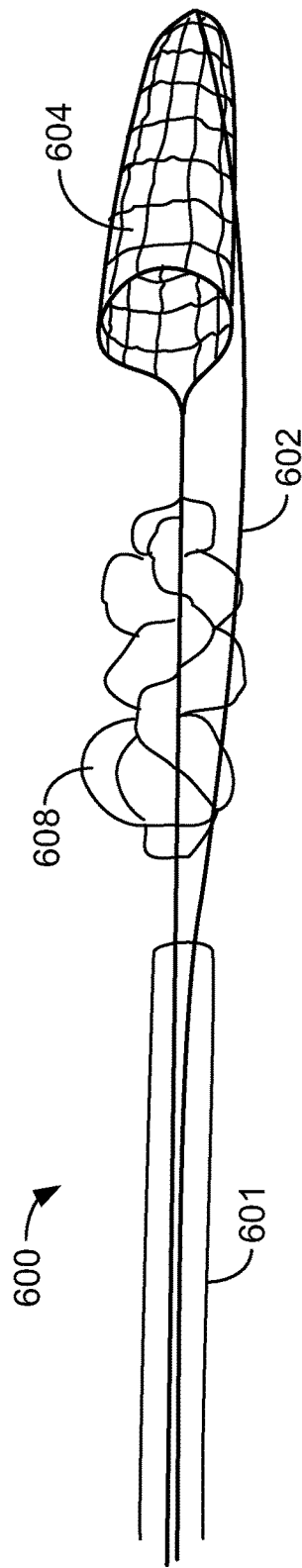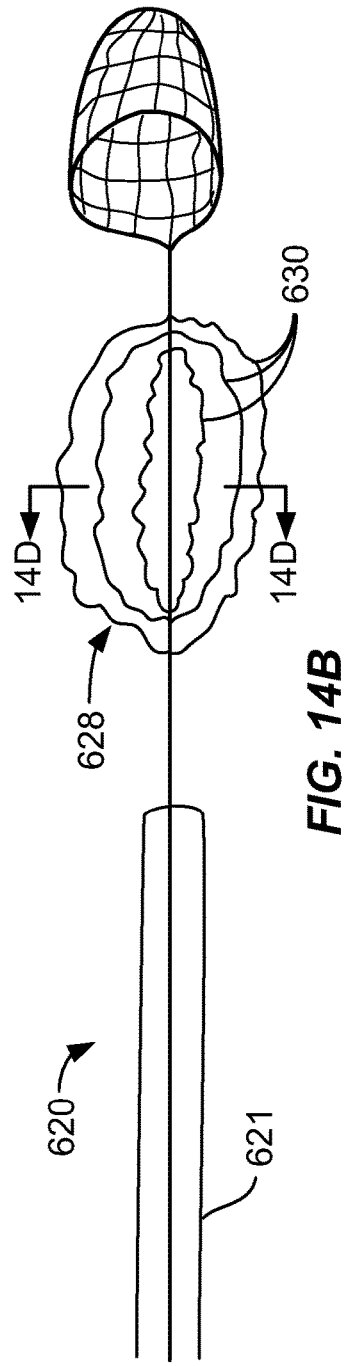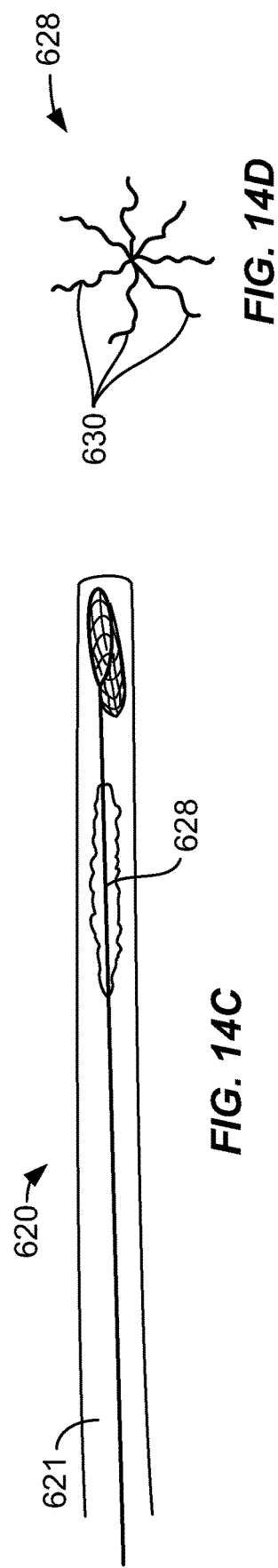

CLOT RETRIEVERS AND METHODS FOR DEPLOYMENT

CROSS-REFERENCE TO RELATED APPLICATION

This application claims the benefit of U.S. Provisional Application No. 62/672,383, filed on May 16, 2018; this application is also a continuation-in-part of PCT/US2017/066789, filed on Dec. 15, 2017, which claims the benefit of U.S. Provisional Application No. 62/436,920, filed on Dec. 20, 2016, the full disclosures of each of these prior applications are incorporated herein by reference.

BACKGROUND OF THE INVENTION

1. Field of the Invention

The present invention relates generally to medical devices and methods, and more particularly, to devices and methods for mechanically removing unwanted occlusive material from a blood vessel.

Coronary vessels can become narrowed or occluded by plaque or thrombus causing myocardial infarction, angina, and other conditions. For example, a coronary stenosis can be formed by an atheroma, which is typically a harder, calcified substance that forms on the lumen walls of a blood vessel. A stenosis can also be formed of a thrombus material, which is typically much softer than an atheroma, but can nonetheless cause restricted blood flow in the lumen.

A number of medical procedures have been developed to effect removal or displacement of plaque or thrombus from vessel walls to open a channel restoring blood flow. Conventional catheter-based removal techniques include enzymatic dissolution of the stenotic lesion, such as with streptokinase, and energy-based ablation, for example, by radio frequency signals and lasers. Removal of a stenosis has also been achieved by thrombectomy or atherectomy. During thrombectomy and atherectomy, the stenosis is mechanically cut or abraded away from the vessel.

Complications can arise from stenosis removal procedures. Stenotic debris, once separated from the stenosis, can flow from the treatment site though the vessel and compromise blood flow at a location removed from the treatment site. Various protection systems have been developed to prevent such debris from embolizing in a vessel following treatment. One such technique includes shredding the debris into sufficiently small fragments such that they will not occlude vessels within the vasculature. However, it can be difficult to control the size of severed fragments, particularly for thrombi, which tend to dislodge in larger fragments than atheroma. Another technique includes introducing negative pressure into the vessel during treatment to vacuum up dislodged stenotic debris. However, excessive negative pressure can cause the vasculature to collapse.

Yet another technique for eliminating incidental stenotic debris during treatment includes introducing a vascular filter distal from the stenosis before removal. The filter can catch dislodged fragments of the stenosis as they flow downstream from the treatment site. Later, the vascular filter can be retrieved along with the caught debris after the removal of the stenosis at the treatment site is complete.

Such filters include various configurations of nets, baskets, and other capture mechanisms for grabbing stenotic debris. However, low-profile delivery to and deployment of captures devices at a treatment site in a blood vessel can be difficult to achieve. Many conventional designs are hindered by complex and cumbersome actuation mechanisms. Moreover, captured stenotic debris can become loose again during extraction and retrieval of the capture device, again posing a risk of becoming dangerous emboli.

2. Description of Background Art

Devices related to removal of occlusive material from blood vessels are described in U.S. Pat. Nos. 9,402,708; 9,351,749; 7,695,491; and 6,001,118; and U.S. Patent App. Pub. Nos. 2016/0220346; 2016/0192956; and 2016/0143722.

SUMMARY OF THE INVENTION

The present invention provides medical devices and methods for removing harmful occlusive material, such as soft plaque, calcified plaque, thrombus, fibrin, clot, fatty tissue, etc., (generally referred to herein as "clot" material) from blood vessels and other body lumens Blood vessels, including the coronary, pulmonary, and peripheral vasculature are often treated with catheter-based thrombectomy or atherectomy procedures. Aspects of the present invention improve the reliability and efficacy of such procedures by enabling low-profile delivery of clot retrieval devices inside a blood vessel, and providing simple and reliable mechanisms for deploying and retrieving the same. Various configurations of clot capture mechanisms are described herein for capturing and extracting clot material. Generally, the present invention provides a set of catheters or tubes containing a collapsed or compressed clot capture net, funnel, and/or other clot capture mechanisms which may be advanced distally through a blood vessel and past a clot region by a net shaft or deployment wire. Once in place, the net shaft is retracted proximally, deploying the expanding clot capture mechanism which then entrains and captures clot material as the device is removed from the vasculature.

In a first aspect, the present invention provides a method for retrieving clot from a blood vessel. In one example, the method includes advancing a delivery tube or catheter in a distal direction through a blood vessel or other body lumen toward and past a clot region in the blood vessel. The blood vessel is a typically a coronary artery, peripheral vein, or peripheral artery, but can also be other types of vasculature such as renal, carotid, pulmonary artery, or the like.

With the delivery tube or catheter past the clot region, the method further includes advancing a net shaft or deployment wire in a distal direction from a distal end of delivery tube or catheter, causing a collapsible hoop integrally formed with or otherwise attached to a distal end of the net shaft or deployment wire to deploy laterally relative to a longitudinal axis of the net shaft or deployment wire as the collapsible hoop emerges from the delivery tube or catheter.

The method further includes drawing or retracting the net shaft or deployment wire in a proximal direction to pass the deployed hoop over and past the region of clot. The deployed hoop pulls an attached clot collection net other capture mechanism which entrains and moves the clot from the region as the net shaft or deployment wire is drawn proximally.

In a further embodiment, advancing the net shaft or deployment wire in a distal direction further deploys a funnel attached to the net shaft or deployment wire. The funnel is aligned on a proximal side of the clot collection net and configured to direct the clot into the clot collection net as the net shaft or deployment wire is drawn in the proximal direction. In other embodiments described below, the funnel may be attached to a separate funnel sheath that is coaxially and slidably disposed over the net shaft or deployment wire.

In yet a further embodiment, the net delivery tube or catheter is initially disposed inside a main delivery tube or outer sheath during delivery. The method includes advancing the main delivery tube or outer sheath in a distal direction through the blood vessel, carrying the net delivery shaft or net delivery shaft or wire delivery tube past the clot region. In some instances, the main delivery tube or outer sheath is attached to a handle assembly with integral sliders to allow a user to manually advance and retract the clot collection net and funnel to perform clot extraction methods according to the present invention.

In a still further embodiment, the main delivery tube or sheath carries a net delivery tube in addition to the net delivery shaft or wire delivery, where the net delivery tube carries at least a portion of the clot collection net. Method of use include pulling the clot collection net from the net delivery tube by drawing the net shaft or deployment wire in a proximal direction. I In some embodiments, one or more of the hoop and funnel are deployed from the net delivery shaft or wire before the clot collection net is advanced or drawn from the net delivery tube. The method may also include retracting the main delivery tube or sheath to expose the net delivery shaft or wire before deployment of the clot capture mechanisms.

In yet a further embodiment, the net delivery tube carrying at least a portion of the clot collection net includes a secondary or stabilizing wire attached to the distal end of the net. The wire allows for the distal end of the net to be directionally controlled, and potentially retracted into the net delivery tube if necessary. For example, a distal-most end of the net may be closed and attached to the net delivery shaft or wire while the proximal-most end of the net is open and peripherally attached to the wire hoop and secondary or stabilizing wire.

In still further embodiments, the net delivery tube carries at least a portion of the clot collection net and includes a catheter with a "J" shaped tip, known in the art as an angiographic catheter, attached to the distal end of the net. The catheter allows for the distal end of the net to be directionally controlled, and potentially retracted into the net delivery tube if necessary. The use of a catheter also allows for the infusion of clot-dissolving drugs into the net surrounding the clot, thus dissolving clots that may be too large, or too hard for extraction. The catheter could also be used to aspirate the portions of the clot that dissolve for easy removal.

In a second aspect, the present invention provides a clot retriever. In one example, the clot retriever includes a net shaft or deployment wire having a distal end and a proximal end. A resiliently collapsible hoop is integrally formed with or otherwise attached to the distal end of the net shaft or deployment wire, and a clot collection net is coupled to the resiliently collapsible hoop. A net delivery sheath is configured to translatably receive the net shaft or deployment wire so that the resiliently collapsible hoop can be moved from a retracted position where the hoop is constrained within the lumen of the net delivery sheath to an advanced position where the hoop is deployed by releasing it from constraint. Once released from constraint, the hoop is configured to deploy laterally outwardly from a main body of the delivery shaft or wire to unfurl the clot collection net.

In a further embodiment, the net shaft or deployment wire comprises a shape memory metal such as nitinol formed into the resiliently collapsible hoop and the main body.

In a still further embodiment, the clot retriever includes a collapsible funnel. The funnel is attached to the main body at a location proximal to the resiliently collapsible hoop. The funnel, when free from constraint and deployed, is tapered to have a clot receiving opening at its proximal end which is larger than a clot directing opening at its distal end.

In yet a further embodiment, the funnel has curved sides. The curved sides are configured to interleave when the funnel is collapsed, pre-deployment, in the net delivery shaft or wire delivery tube. When deployed, the funnel can expand or unfold to a preselected dimension, or to the extent of the lumen of the blood vessel.

In another embodiment, the clot retriever includes a main delivery tube. The main delivery tube has a lumen configured to translatably receive the net delivery shaft or wire delivery tube.

In a further embodiment, the clot collection net everts from a distal end of the net delivery shaft or wire delivery tube. The clot collection net and net delivery shaft or wire are stowed in parallel within the main delivery tube prior to deployment.

In yet a further embodiment, a net delivery tube has a lumen and a distal opening which receives the clot collection net. The net delivery tube is stowed in parallel to the net delivery shaft or wire within the main delivery tube.

In yet a further embodiment, the net is made from a mesh-like material such as Nylon or polyester with mesh porosity sufficient for capture and retainment of clot material.

In yet a further embodiment, the net is made from a compliant plastic material such as polyurethane with a pattern of holes cut or punched in it sufficient for capture and retainment of clot material.

In yet a further embodiment, the clot capture net is shaped such that is can enclose and retain the clot, such shape to be cylindrical, conical, or a combination thereof.

In various embodiments, the net shaft or deployment wire has a length in the range from 10 cm to 250 cm. In one embodiment, the clot collection net is a short net having a length with a length in the range from 0.1 cm to 20 cm. In an alternate embodiment, the net is a long net having a length in the range from 0.1 cm to 20 cm. In another embodiment, the funnel is a short funnel having a length in the range from 0.1 cm to 20 cm. In another embodiment, the funnel comprises a long funnel having a length in the range from 0.1 cm to 20 cm. It will be obvious to those of skill in the art that various configurations of the net shaft or deployment wire, clot collection net, funnel, and other components may be assembled based on the parameters of the delivery catheter or tube and to suit the characteristics of the blood vessel and clot to be removed.

In a still further aspect, the present invention provides a clot retriever system comprising a shaft assembly which includes a net deployment shaft, a clot collection net, and a funnel sheath. The net deployment has a distal end, a proximal end, and a resiliently collapsible hoop coupled to the distal end of the shaft. The clot collection net is secured to the resiliently collapsible hoop. The funnel sheath has a readily collapsible funnel at its distal end and a lumen configured to translatable receive the net deployment shaft. In this way, the resiliently collapsible hoop can be moved from a retracted position where the hoop is constrained within the lumen of the funnel shaft to an advanced position where the hoop is released from such constraint and deploys laterally outwardly from the main body of the net deployment shaft to unfurl the clot collection net.

Usually, the clot retriever system will further comprise a handle assembly. The handle assembly typically includes a handle body having a distal end and a proximal end, and an outer sheath fixedly attached to the distal end of the handle body where the shaft assembly is disposed within a central lumen of the out sheath.

The handle assembly typically further comprises a funnel slide, a net slide, and a net deployment slide. Each of the slides are slideably disposed on or over an exterior of the handle body so that they may be axially reciprocated by a user, typically using a single hand. The funnel slide is attached to the funnel sheath to axially reciprocate the funnel sheath between a distally extended position where the funnel can self-open as it emerges from a distal end of the outer sheath and a proximally recurrent position where the funnel closes as it is drawn back into the distal end of the outer sheath. The net sheath slide is attached to the net sheath to axially reciprocate the net sheath between a distally extended position where a distal end of the net sheath is positioned distally beyond the funnel when the funnel is opened in a proximally retracted position where the net sheath is within a lumen of the funnel sheath. The net deployment slide is attached to the net deployment shaft to axially reciprocate the net deployment shaft between a distally extended position where the net self-opens as it emerges from a distal end of the net sheath in a proximally retracted position where the net at least partially closes as it is drawn back into the funnel of the funnel sheath.

While particularly suitable for percutaneous intravascular procedures as performed in catheter labs by interventional physicians, the devices and methods of the present invention will also find use in hybrid operating rooms under imaging guidance where surgeons and interventional cardiologists work jointly as well as in open surgical procedures under direct vision by operating surgeons.

Other objects and advantages of the present invention will become apparent from the detailed description to follow, together with the accompanying drawings.

BRIEF DESCRIPTION OF THE DRAWINGS

The foregoing and other objects, features and advantages of embodiments of the present inventive concepts will be apparent from the more particular description of preferred embodiments, as illustrated in the accompanying drawings in which like reference characters refer to the same or like elements. The drawings are not necessarily to scale, emphasis instead being placed upon illustrating the principles of the preferred embodiments.

FIG. 12A illustrates the clot retrieval device retracted fully within an aspiration tube. FIG. 12B illustrates the clot retrieval device partially advanced from the aspiration tube. FIG. 12C illustrates the clot retrieval device retracted fully within an aspiration tube. FIG. 12D illustrates use of a wire to initially deploy a clot retrieval net of the clot retrieval device. FIG. 12E illustrates use of a wire to further deploy the clot retrieval net of the clot retrieval device. FIG. 12F illustrates use of the wire to fully deploy the clot retrieval net of the clot retrieval device.

FIGS. 13A and 13B illustrate a fifth clot retrieval device embodiment having a single outer delivery/aspiration tube and a self-expanding helical clot retrieval member constructed in accordance with the principles of the present invention. FIG. 13A shows the helical self-expanding clot retrieval member constrained inside the delivery/aspiration tube. FIG. 13B shows the helical self-expanding clot retrieval member expanded after being advanced distally out of the delivery/aspiration tube.

FIGS. 14A through 14D illustrate additional clot retrieval device embodiments in accordance with the principles of the present invention. FIG. 14A shows a clot retrieval catheter having a single outer delivery/aspiration tube with a self-expanding clot retrieval member similar to the clot retrieval catheter of FIG. 13 and having a longer net. FIG. 14B show a clot retrieval catheter having a single outer delivery/aspiration tube with a self-expanding clot retrieval member including a plurality of radially oriented splines. FIG. 14C shows the self-expanding clot retrieval member of FIG. 14B retracted into the single outer delivery/aspiration tube. FIG. 14D is a cross-sectional view taken along line 14D-14D of FIG. 14B.

FIG. 15B is a longitudinal cross-sectional view of an outer delivery/aspiration tube having a shaft therein. FIG. 15A is a cross-sectional view taken along line 15A-15A of FIG. 15B. FIG. 15C shows a mesh-like a clot retrieval net 704 on the shaft. The mesh-like a clot retrieval unfolds from from a "closed" position (FIG. 15C) to an ioen configuration as shown in FIG. 15D. A clot reteival basket may be attached to a distal end of the outer delivery/aspiration tube, as shown in FIG. 15E, and the outer delivery/aspiration tube and the shaft carrying the mesh may be assembled as shown in FIG. 15F.

FIG. 18A shows a distal end of an outer sheath of a clot retriever being advanced in a lumen of the blood vessel to a location on one side of a clot. FIG. 18B shows a funnel being deployed from the sheath in the location on the one side of the clot. FIG. 18C shows distal advancement of a net deployment sheath beyond the clot. FIG. 18D shows deployment of a net deployment shaft and a clot retrieval net from a distal end of the net deployment sheath. FIG. 18E shows retraction of the net to close against the funnel to capture thee clot funnel 814. The net and funnel are then retracted back into the outer sheath as shown in FIG. 18F.

DETAILED DESCRIPTION OF THE INVENTION

Figure 1:
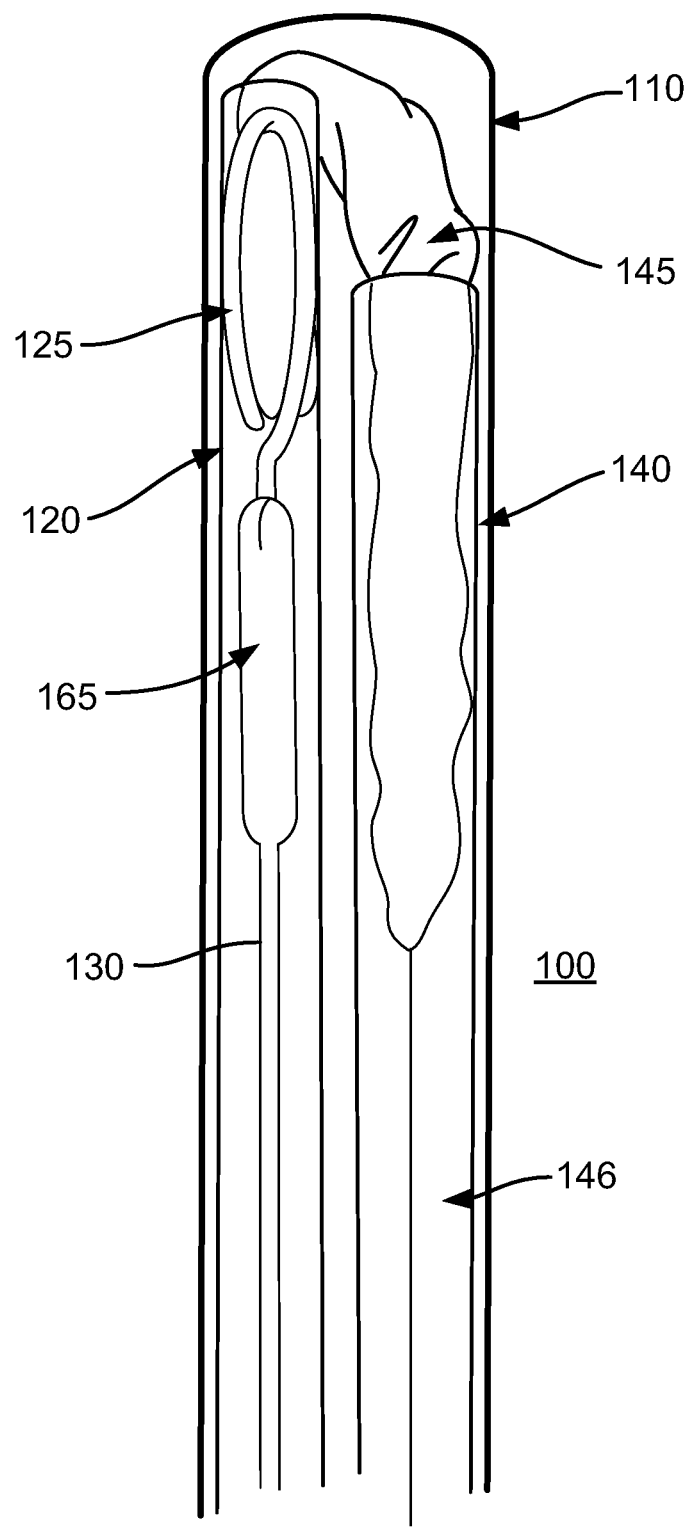
FIG. 1 illustrates a first clot retrieval device, pre-deployment, according to an example embodiment.

FIGS. 1-4 illustrate a first clot retrieval device 100 throughout various stages of deployment. Clot retrieval device 100 comprises a net shaft or deployment wire 130 with a resiliently collapsible hoop 125 formed integrally in a distal end. A clot collection net 145 is coupled to the collapsible hoop 125. Also at a distal end of the net shaft or deployment wire 130 but proximal from the hoop 125 is a collapsible funnel 165. The funnel 165 has curved sides configured to interleave while the funnel is collapsed inside the net delivery shaft or wire delivery tube.

In the pre-deployment configuration of the clot retrieval device 100, as shown in FIG. 1, the hoop 125 is initially collapsed and disposed within the net delivery shaft or wire delivery tube 120. The net shaft or deployment wire 130 is also translatably received by the net delivery shaft or wire delivery tube 120. Similarly, the clot collection net 145 is initially disposed at least partially in within a net delivery tube 140. The funnel 165 is also collapsed within the net delivery shaft or wire delivery tube 120. Both the net delivery shaft or wire delivery tube 120 and net delivery tube 140 are disposed within a main delivery tube 110. There may also be included a wire or tube 146 distally attached to the clot collection net such that the net can be positioned therefrom, or retrieved into the net delivery tube. In it's tube configuration, the tube can be used also to infuse or aspirate into and from the net enclosed space.

Figure 2:
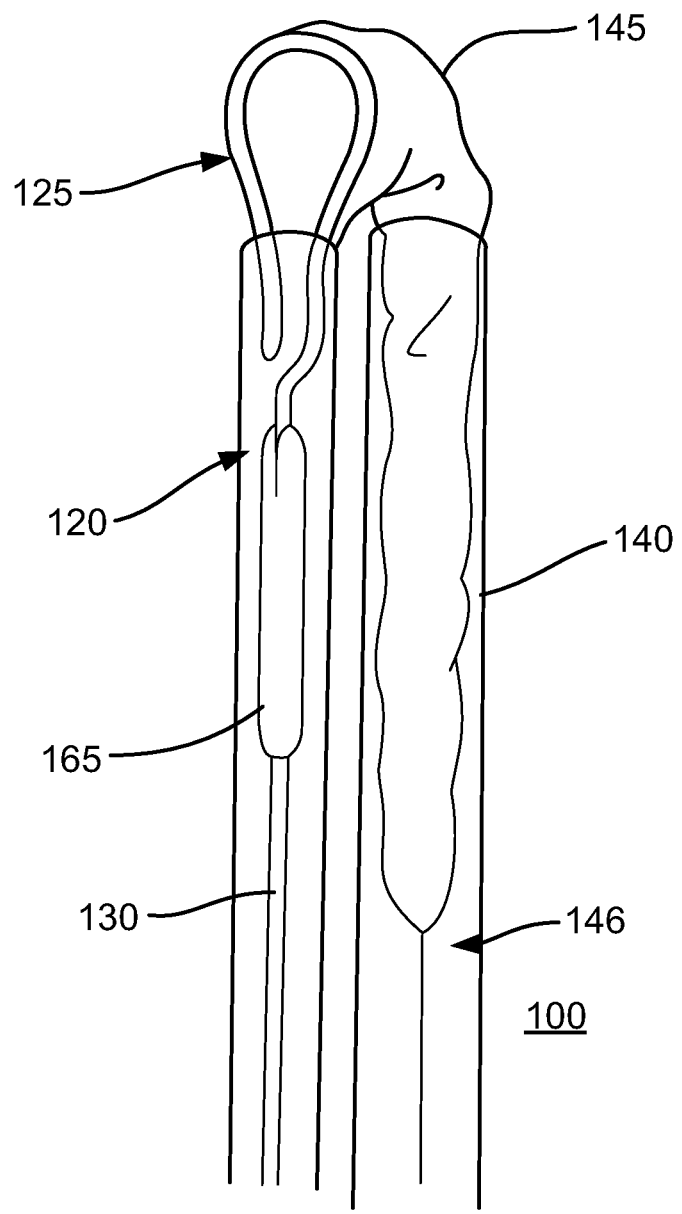
FIG. 2 illustrates the first clot retrieval device, mid-deployment, according to an example embodiment.
Figure 3:
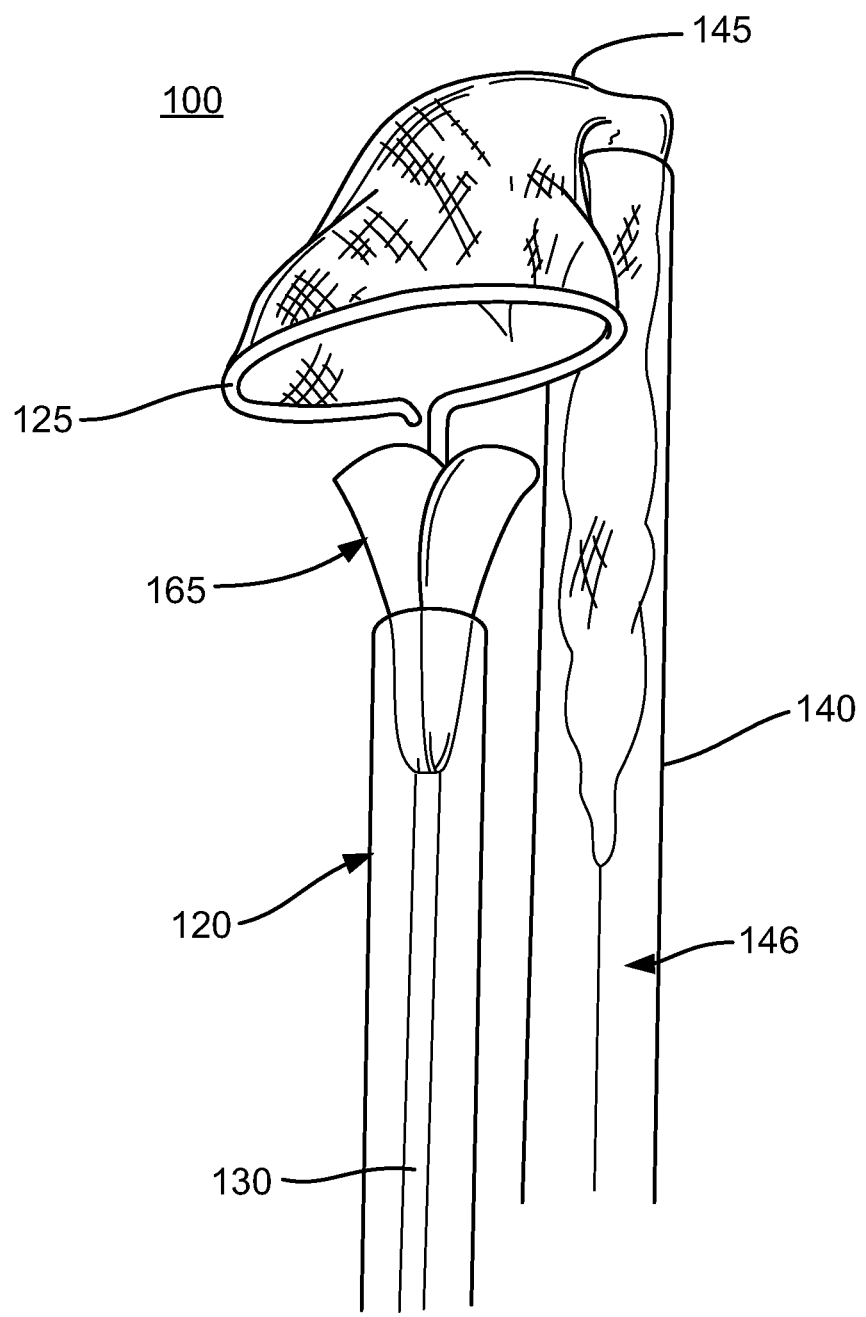
FIG. 3 also illustrates the first clot retrieval device, mid-deployment, according to an example embodiment.
Figure 4:
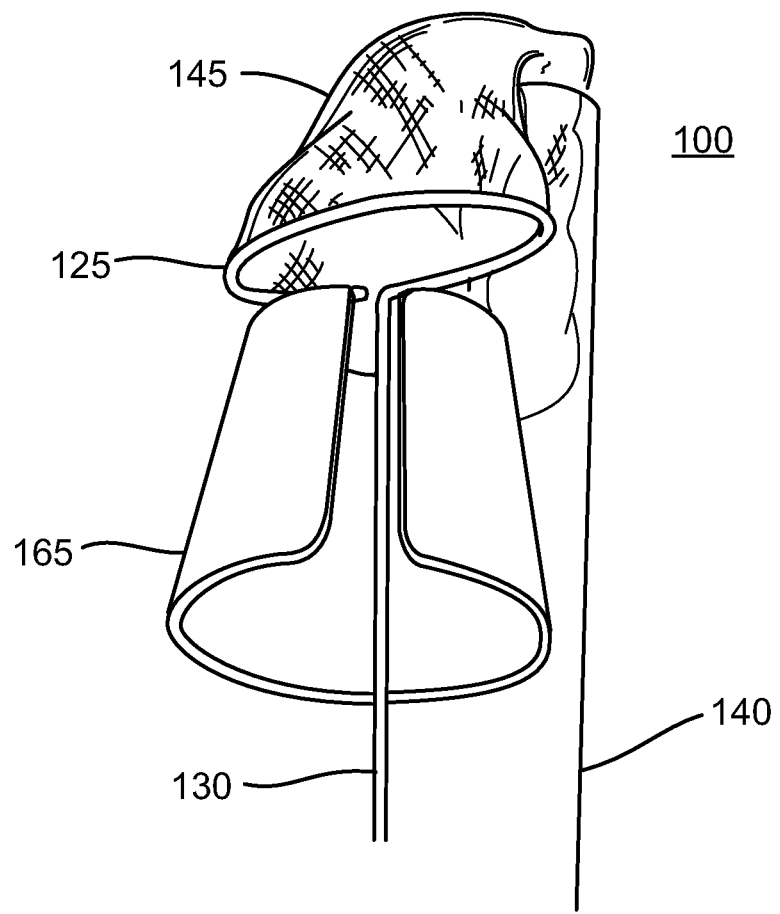
FIG. 4 illustrates the first clot retrieval device, post-deployment, according to an example embodiment.

During deployment of the clot retrieval device 100, as shown in FIG. 2, the main delivery tube is retracted to expose the net delivery shaft or wire delivery tube and net delivery tube 140. The net delivery shaft or wire delivery tube is itself retracted (or the net shaft or deployment wire 130 otherwise advanced in a distal direction through the net delivery shaft or wire delivery tube 120) allowing the resiliently collapsible hoop 125 to emerge from the distal end of the net delivery shaft or wire delivery tube 120. As shown in FIG. 4, once a critical portion of the resiliently collapsible hoop 125 is no longer constrained by net delivery shaft or wire delivery tube, the hoop 125 expands laterally relative to a longitudinal axis of the net shaft or deployment wire 130. As the net shaft or deployment wire continues to advance, the funnel 165 may also emerge from the net delivery shaft or wire delivery tube. As the funnel emerges, it expands or unfurls.

After deployment of the clot retrieval device 100, as shown in FIG. 4, the funnel has expanded to a stable configuration for entraining and directing occlusive material to the clot collection net 145. In some configurations, a proximal opening of the funnel can be larger than a distal opening of the funnel to more effectively guide clot material into the clot collection net 145. In another configuration the distal opening of the funnel can be smaller than the opening of the deployed hoop 125.

FIGS. 5-8 illustrate removal of a clot 190 in a blood vessel 180 with the clot retrieval device. After the clot retrieval device is introduced to the blood vessel 180, the main delivery tube is advanced past a clot region. The hoop 125 and funnel of the clot retrieval device are then deployed and the net shaft or deployment wire is retracted to advance the funnel 165 and hoop 125 in a proximal direction of the blood vessel back towards the clot region.

Figure 5:
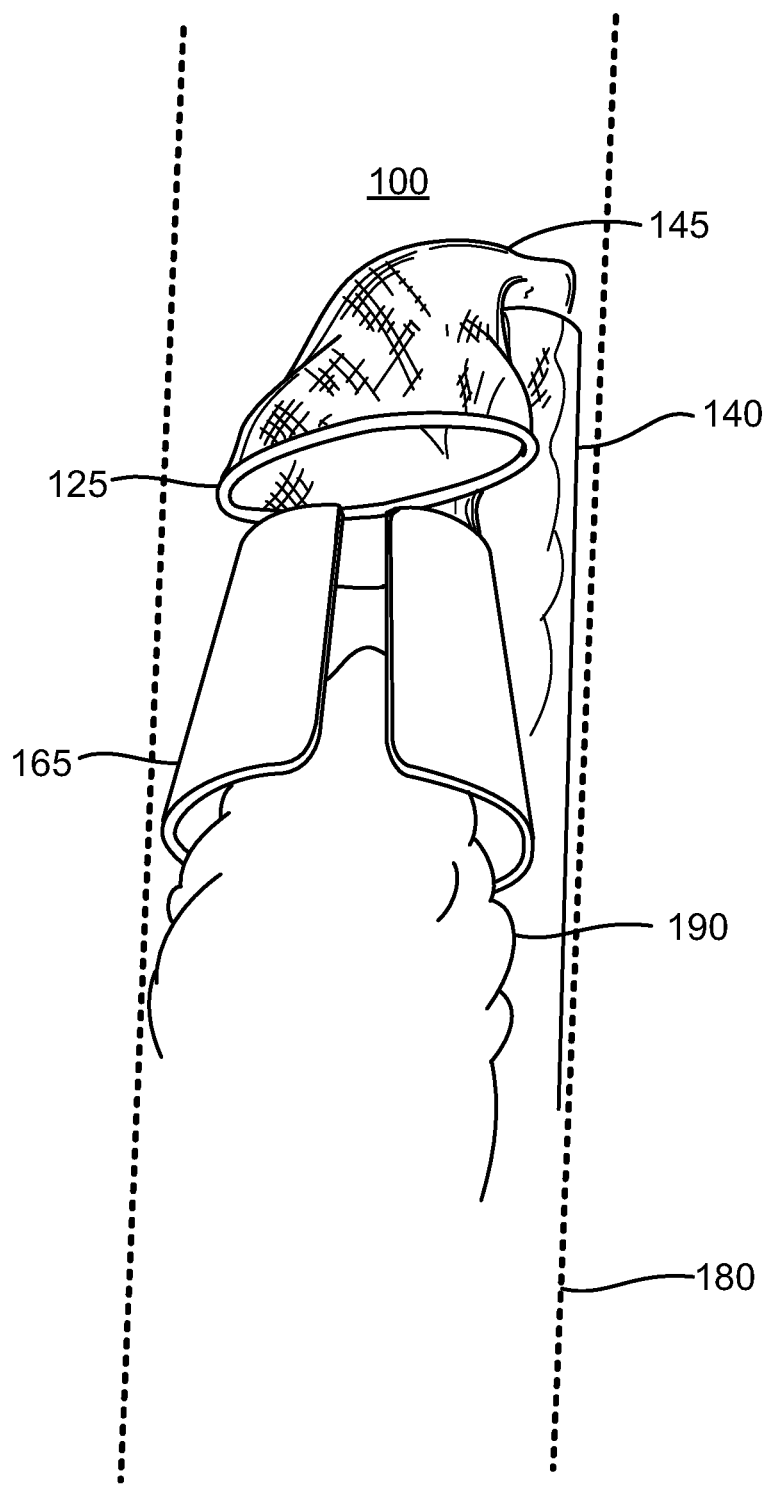
FIG. 5 illustrates the first clot retrieval device entraining a clot in a blood vessel, according to an example embodiment.
Figure 6:
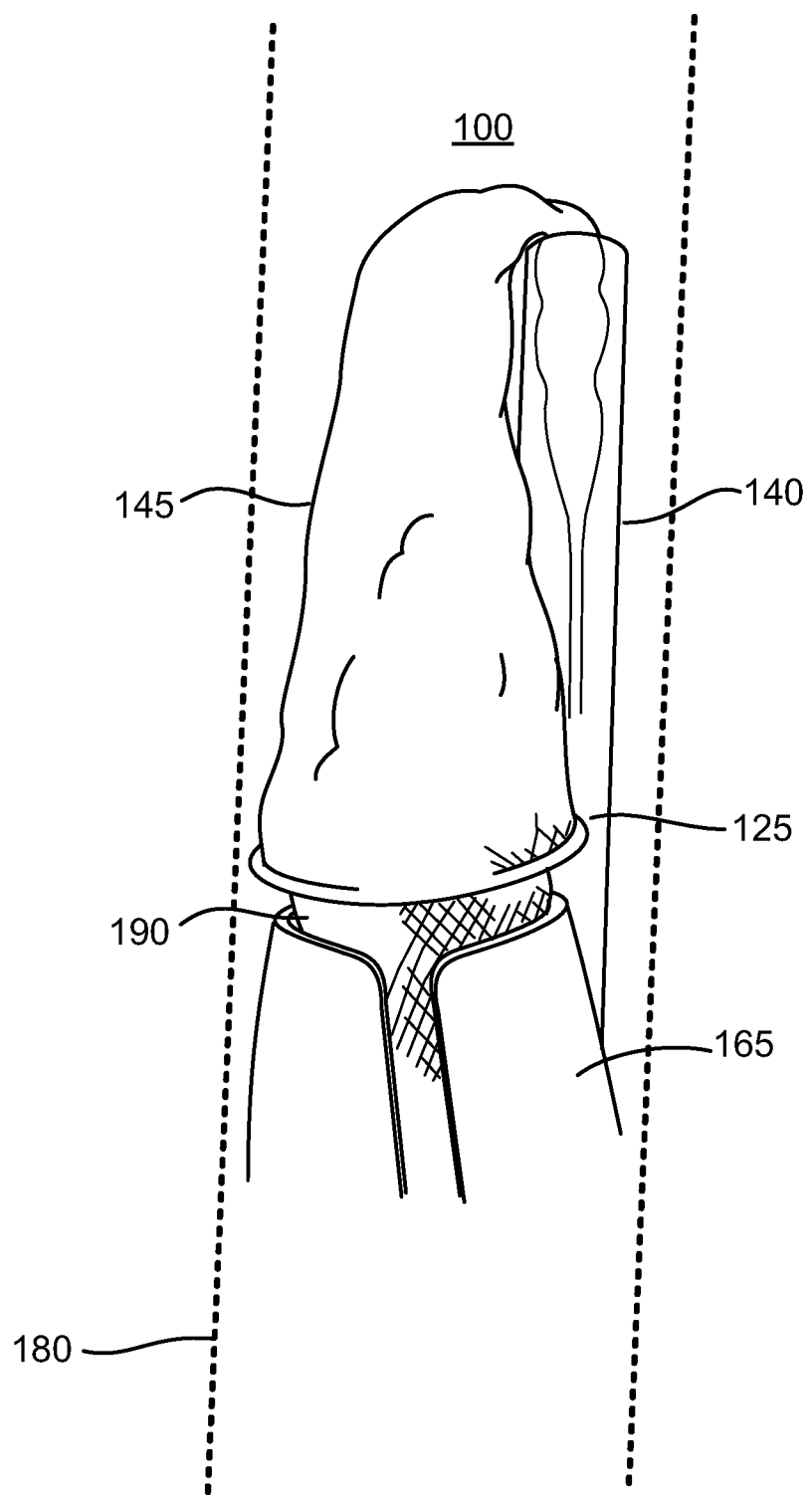
FIG. 6 illustrates the first clot retrieval device capturing the clot in the blood vessel 180, according to an example embodiment.
Figure 7:
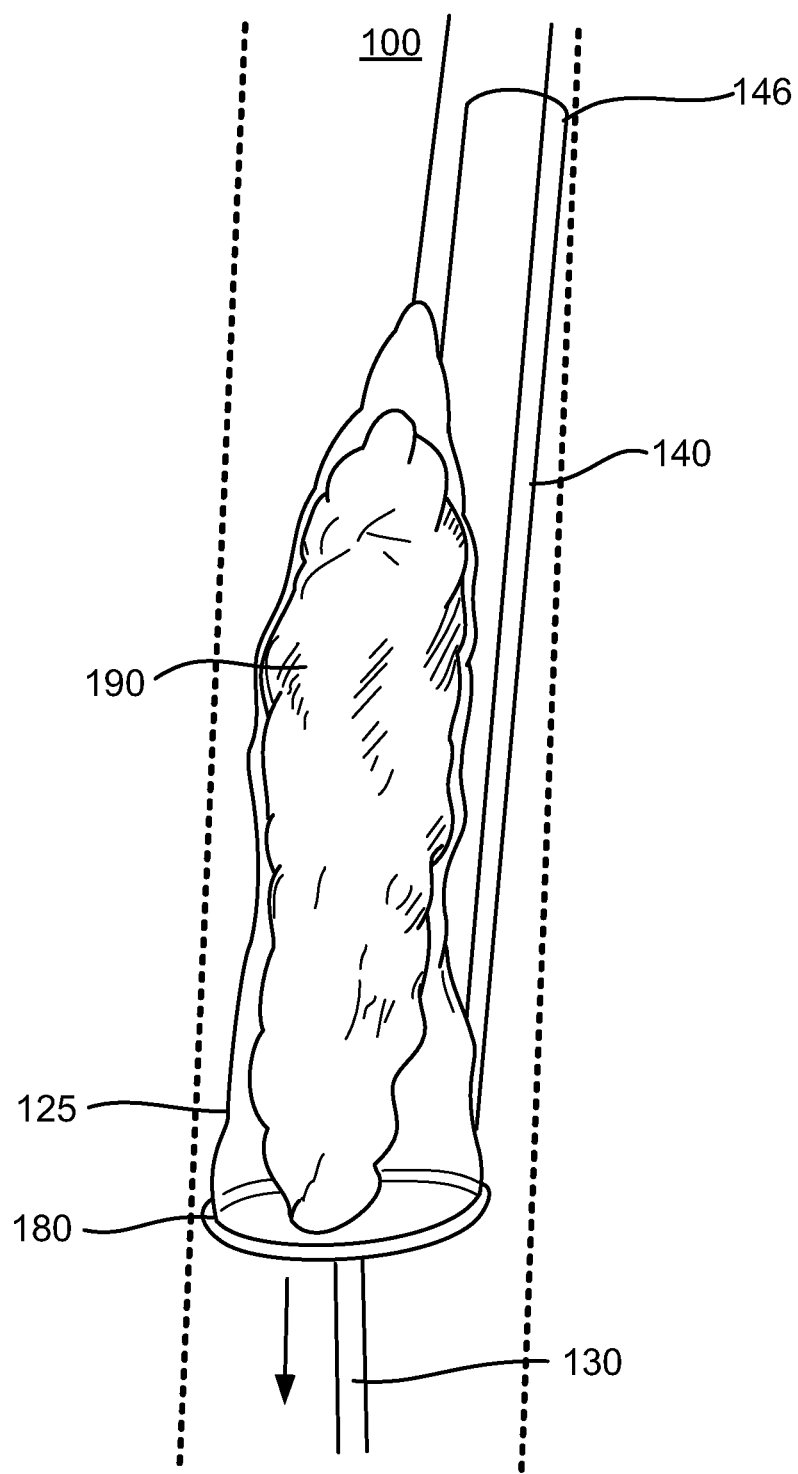
FIG. 7 illustrates the first clot retrieval device retrieving the clot in the blood vessel 180, according to an example embodiment.
Figure 8:
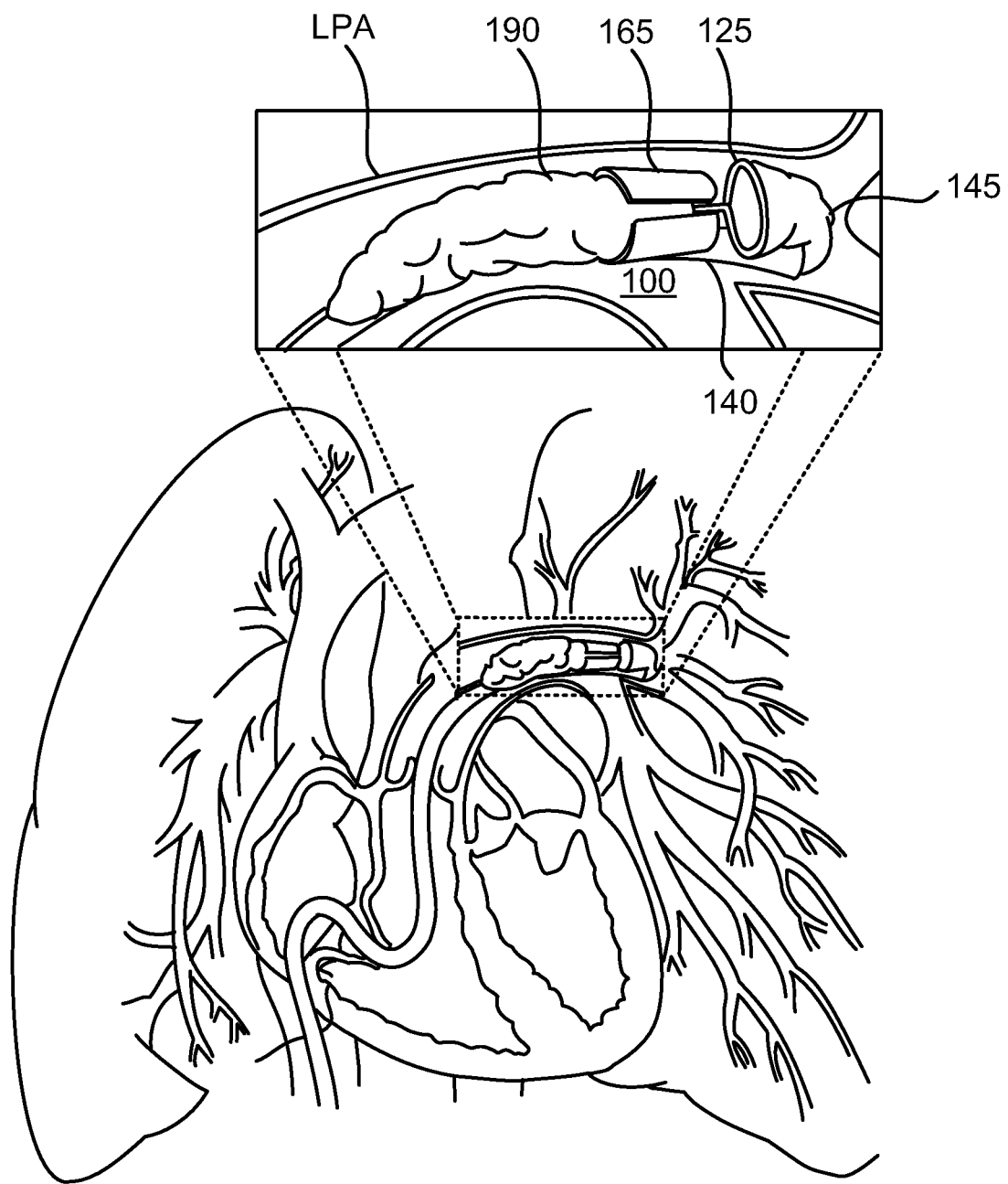
FIG. 8 illustrates the first clot retrieval device capturing a clot in a left pulmonary artery according to an example embodiment.

As shown in FIG. 5, a first portion of the clot 190 is entrained by the funnel as the net shaft or deployment wire is retracted in a proximal direction. The funnel guides the clot into the resiliently collapsible net 145 as shown in FIG. 6. As the net shaft or deployment wire continues to retract, the clot passes through the funnel and into the net 145. The net shaft or deployment wire is further retracted until the net 145 and clot are pulled out of the blood vessel. In some embodiments, the net 145 may completely emerge from the net delivery tube 140, as shown in FIG. 7. The net delivery tube 140 may then be retracted before the clot is engaged by the funnel 165 and/or hoop 125. There may also be included a wire or tube 146 distally attached to the clot collection net such that the net can be positioned therefrom, or retrieved into the net delivery tube. The addition of the wire or tube provides the user the option of retracting the net into the delivery tube, or of infusing drugs into the net space, which could include clot busting drugs to soften hard clots. FIG. 8 illustrates the first clot retrieval device capturing a clot in a left pulmonary artery LPA.

Figure 9:
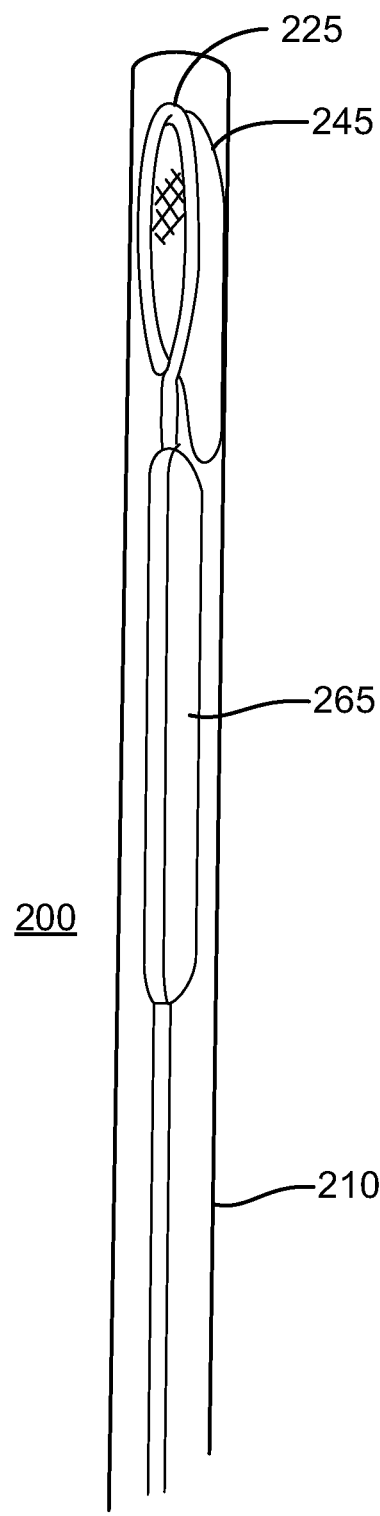
FIG. 9 illustrates a second clot retrieval device, pre-deployment, according to an example embodiment.
Figure 10:
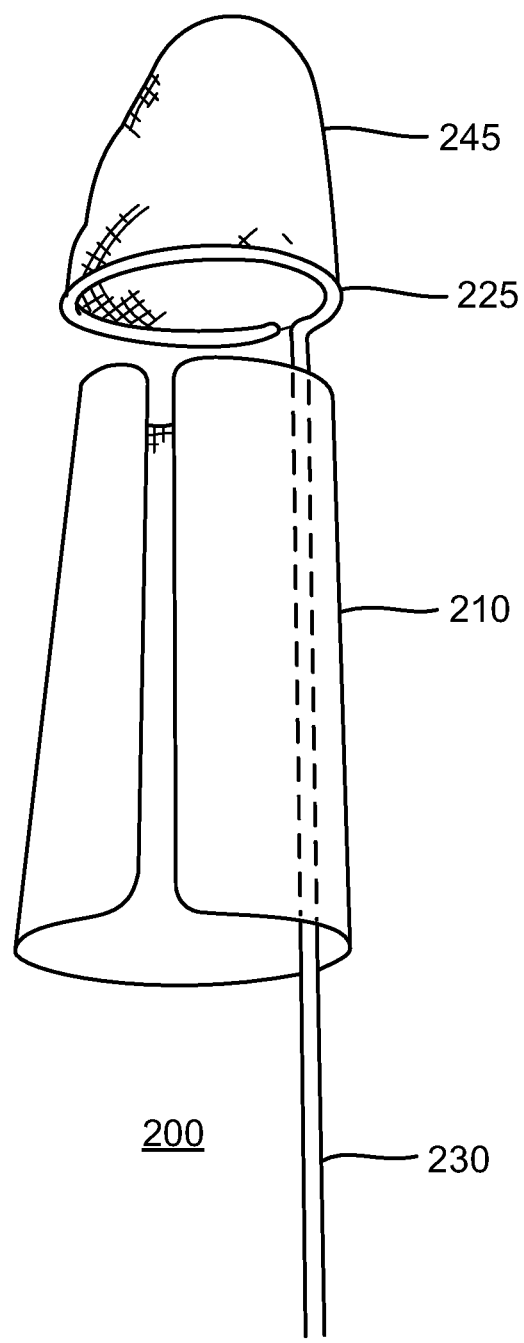
FIG. 10 illustrates a second clot retrieval device, post-deployment, according to an example embodiment.

FIGS. 9-10 illustrates a second clot retrieval device 200 before and after deployment. Like the first clot retrieval device 100, the second clot retrieval device comprises a net shaft or deployment wire 230 with a resiliently collapsible hoop 225 formed integrally in a distal end. A clot collection net 245 is coupled to the collapsible hoop 225. Also at a distal end of the net shaft or deployment wire 230 but proximal from the hoop 225 is a collapsible funnel 265. The funnel 265 has curved sides configured to interleave while the funnel is collapsed inside the net delivery shaft or wire delivery tube.

In the pre-deployment configuration of the clot retrieval device 200, as shown in FIG. 9, the hoop 225 and funnel 265 are initially collapsed and both disposed within the net delivery shaft or wire delivery tube 265 along with the clot collection net 245. Accordingly, in one embodiment, the second clot retrieval device has only a single catheter or tube for carrying the capture mechanisms. In the post-deployment configuration of the clot retrieval device 200, as shown in FIG. 10, the net 245, hoop 225, and funnel 265 each emerge from the deployment tube as the net shaft or deployment wire 230 is retracted in a proximal direction. Once deployed, the second clot retrieval device 200 entrains and retrieves a clot in a similar manner as the first clot retrieval device 100.

Figure 11:
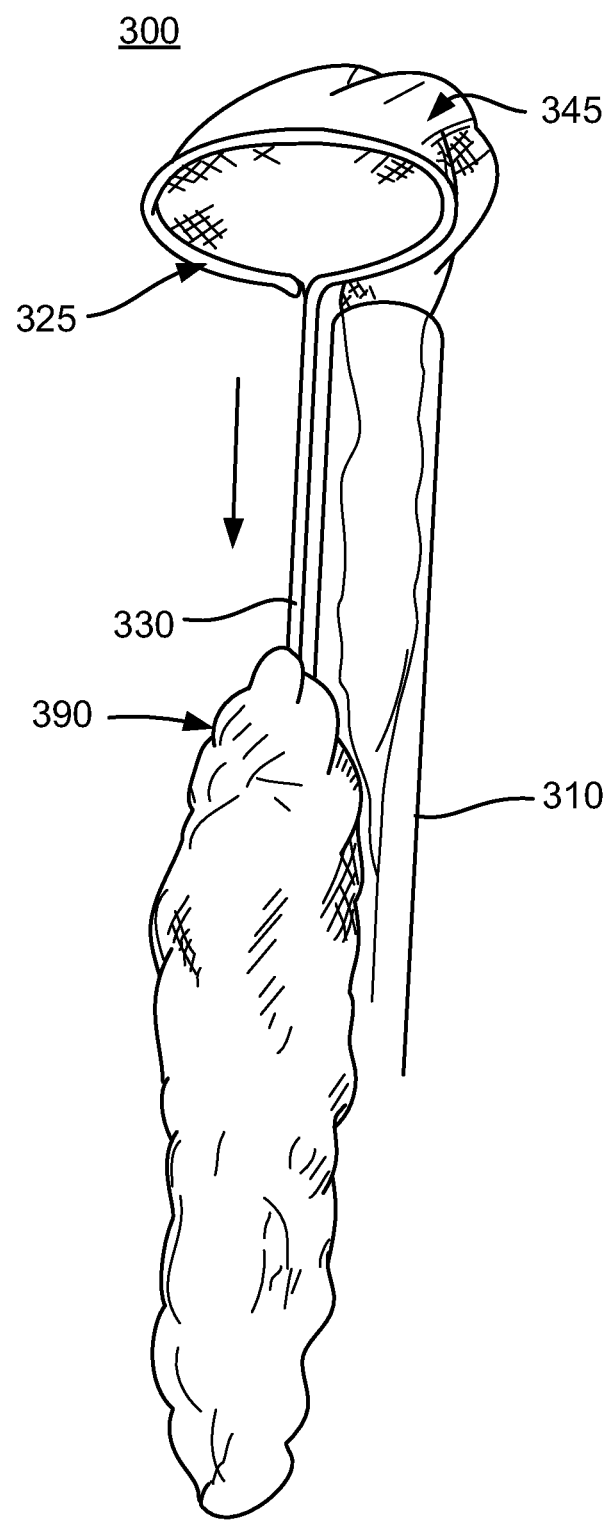
FIG. 11 illustrates a third clot retrieval device, post-deployment, according to an example embodiment.
Figure 12A:
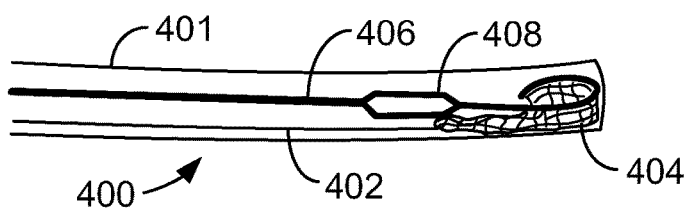
FIGS. 12A through 12F illustrate use of a fourth clot retrieval device having a single outer delivery/aspiration tube embodiment in accordance with the principles of the present invention.
Figure 12B:
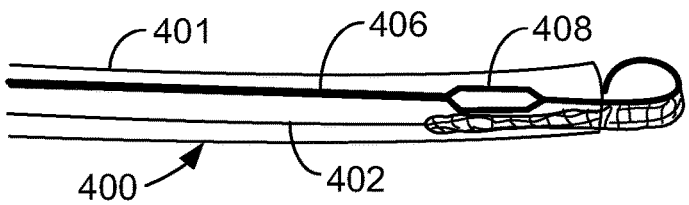
Figure 12C:
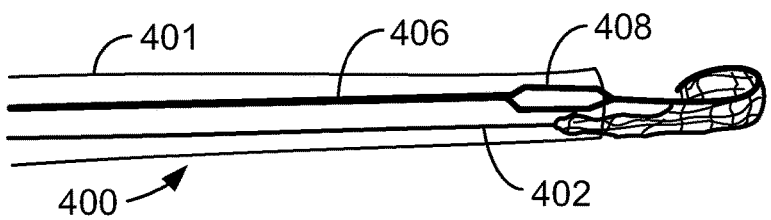
Figure 12D:
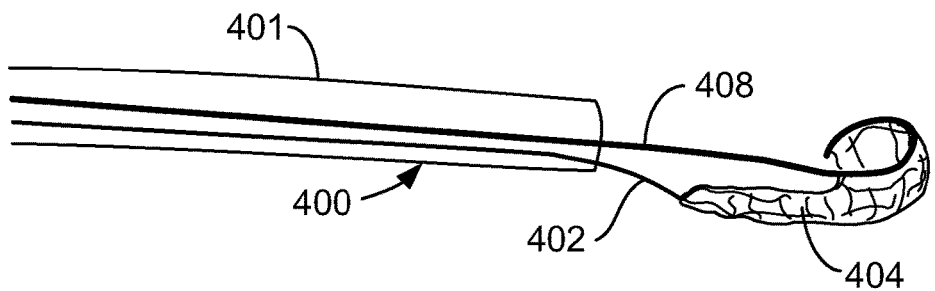
Figure 12E:
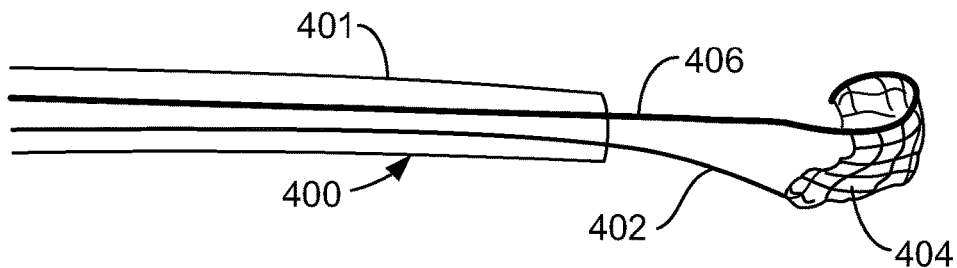
Figure 12F:
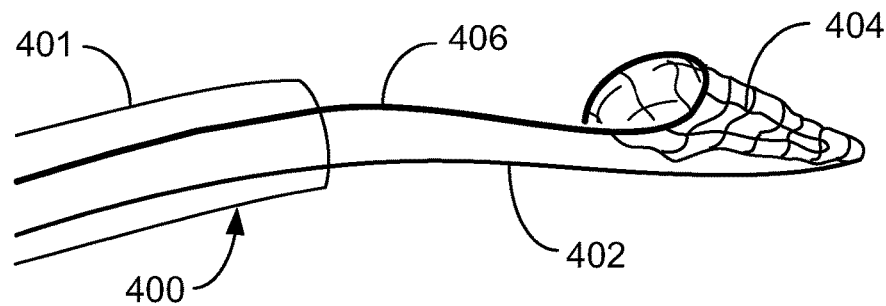

FIG. 11 illustrates a third clot retrieval device 300. The clot retrieval device comprises a resiliently collapsible hoop 325 coupled to a clot collection net 345 which are both disposed in a single tube until deployment. The hoop 325 and net 345 are deployed by advancing a net shaft or deployment wire 330 in a distal direction. Although the third clot retrieval device 300 omits a funnel for guiding a clot 390 into the clot collection net 345, the clot may still be entrained and retrieved by the clot collection net when the net shaft or deployment wire is retracted in a proximal direction after deployment.

It will be obvious to those of skill that additional embodiments comprising various configurations of catheters, funnels, nets, and other components beyond those described in detail above are contemplated and within present invention. For example, the long clot collection net of the first clot retrieval device 100, as shown in FIG. 7, may be substituted for the short net of the second clot retrieval device, as shown in FIG. 10, and vice versa. Ranges of suitable sizes for various components are described hereinabove.

The method comprises advancing a net delivery shaft or wire delivery tube in a distal direction through a blood vessel and past or through a clot region. A net shaft or deployment wire is then advanced in a distal direction from a distal end of the net delivery shaft or wire delivery tube to deploy the collapsible hoop on the distal side of the clot region. The net shaft or deployment wire is then drawn in a proximal direction to pass the deployed hoop over and past the region to direct the clot into the clot collection net. Optionally. The clot is directed into the net by the funnel.

FIGS. 12A through 12F show a clot retrieval catheter 400 having a single outer delivery/aspiration tube 401 in contrast to the two-tube systems previously described. A wire 402 is attached to a distal tip of a clot retrieval net 404 which is disposed at a distal end of an advancement shaft 406 in order to control the shape and form of the net, e.g. to orient the net in-line with an axial segment or length of the a blood vessel and to inhibit the net from folding over on itself, as the net is distally advanced from the outer delivery/aspiration tube 401, as shown in FIGS. 12B through 12E. A proximal end of the outer delivery/aspiration tube 401 may be attached to a vacuum or other aspiration source (not shown) in order to draw clot and thrombus proximally through the tube 401 after the clot/thrombus is pulled into the tube by proximal retraction of the shaft 406. Optionally, a balloon, cage, basket or other retrieval member 408 may be disposed on the shaft 406 proximal of the clot retrieval net 404 (See FIGS. 12A-12C), where the retrieval member 408 will first engage clot/thrombus as the shaft 404 is proximally retracted to pull the member through a region of clot/thrombus and into an open distal end of the outer delivery/aspiration tube 401. In such cases, the clot retrieval net 404 may serve primarily to prevent fragments of the clot and thrombus to be released into circulation during a procedure.

FIGS. 13A and 13B show another embodiment of a clot retrieval catheter 500 having a single outer delivery/aspiration tube 501 constructed in accordance with the principles of the present invention. A self-expanding clot retrieval member 508, typically formed as a helical or other coil, is initially constrained inside the delivery tube 501 and then released by distally advancing shaft 506 to extend the retrieval member beyond the distal end of the tube. A net 504 is secured to a distal end of the shaft 506, where the net may be shorter than in prior designs. A self-expanding wire loop 510 may be attached around a proximal periphery of the net 504 to open the proximal end on the net as the net is advanced distally from the tube 510. In this way, the clot retrieval member 508 initially engages and dislodges the clot which may be aspirated in an open distal end of the delivery/aspiration tube 501 while the net collects any emboli resulting from fragmentation of the clot as it is being retrieved by the clot retrieval member 508.

FIGS. 14A through 14D show still further embodiments of clot retrieval catheters having a single outer delivery/aspiration tube 601 constructed in accordance with the principles of the present invention. FIG. 14A shows a clot retrieval catheter 600 having a single outer delivery/aspiration tube 601 with a self-expanding clot retrieval member 608 similar to the clot retrieval catheter 500 of FIG. 13. Net 604, however, is longer than net 504 and, in order to manage the longer net, a relatively still control wire 602 is attached to a distal end of the net to axially extend and retract the net as desired. Typically, longer nets, such as net 604, may have a length in the range from 5 mm to 200 mm while shorter nets, such as net 504, may have a length in the range from 3 mm to 30 mm.

FIGS. 14B and C show a clot retrieval catheter 620 having a single outer delivery/aspiration tube 611 with a self-expanding clot retrieval member 608 similar to the clot retrieval catheter 500 of FIG. 13. A primary difference between clot retrieval catheter 620 and clot retrieval catheter 500 is that a self-expanding clot retrieval member 628 comprises a plurality of radially oriented splines 630 (FIG. 14D) rather than the helical structure described previously.

Figure 15A:
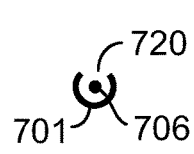
FIGS. 15A through 15F illustrate a seventh two-piece clot retrieval device embodiment in accordance with the principles of the present invention.
Figure 15B:
Figure 15C:
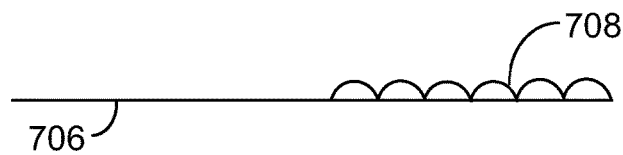
Figure 15D:
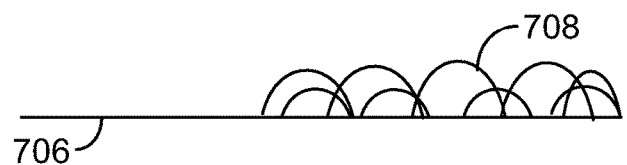
Figure 15E:
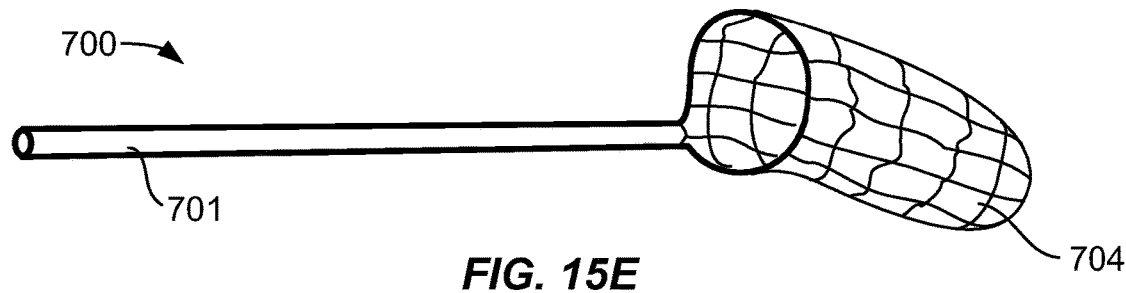
Figure 15F:
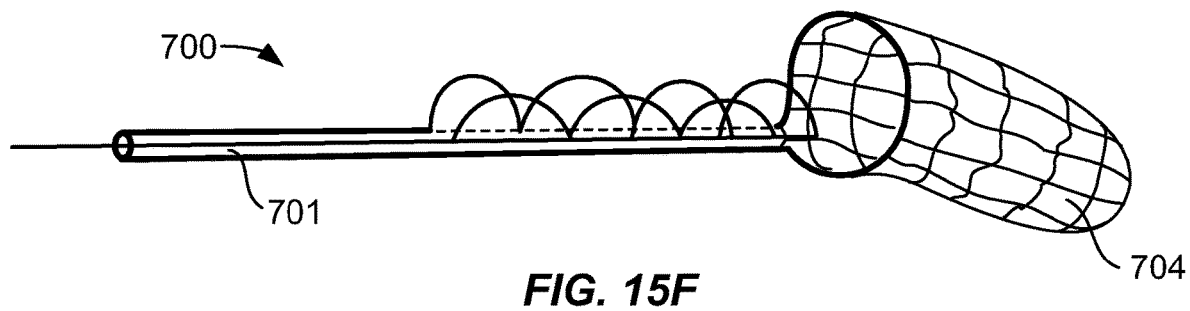

FIGS. 15A through 15F illustrate a two-piece clot retrieval catheter 700 having a single outer delivery/aspiration tube 701 which carries a clot retrieval net 704 on its distal end. See FIGS. 15E and 15F. A shaft 706 carries a self-expanding clot retrieval member 708 that unfolds from a "closed" position into an "unfolded" position, creating a "mesh-like" structure configured to engage targeted clot, as shown in FIGS. 15C and 15D. The self-expanding clot retrieval member 708 will be constrained within a proximal portion of the outer delivery/aspiration tube 701 but can be released through a slot 720 formed in a distal region of the tube, as shown in FIGS. 15A, 15B, and 15F. By engaging the clot with the mesh from the bottom of the clot, an operator will be better able to engage clot, reduce slippage and direct clot toward the basket 704 in order to retrieve and bring out the clot.

Figure 16:
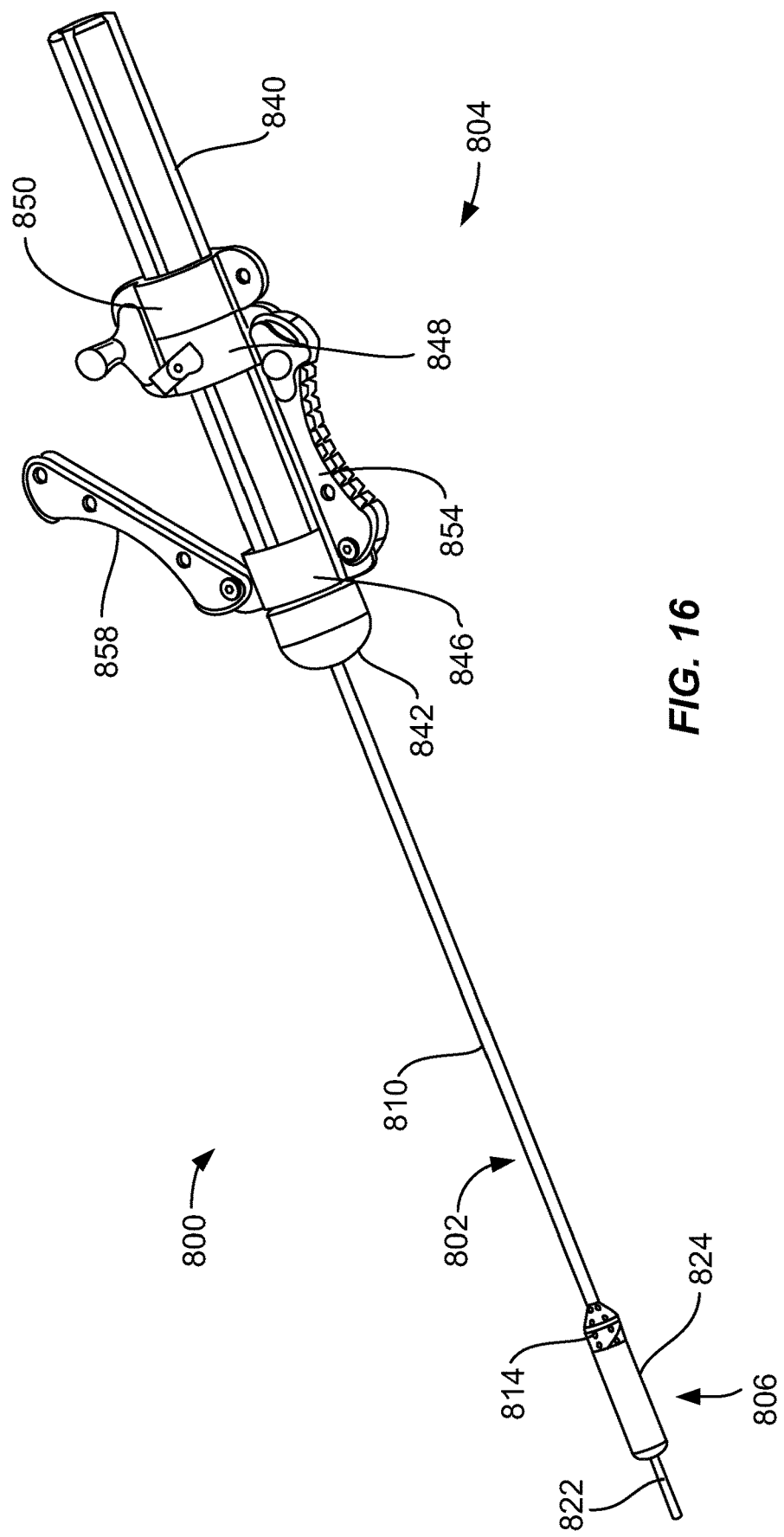
FIG. 16 is a perspective view of an eighth clot retrieval device, post-deployment, according to an example embodiment.
Figure 17:
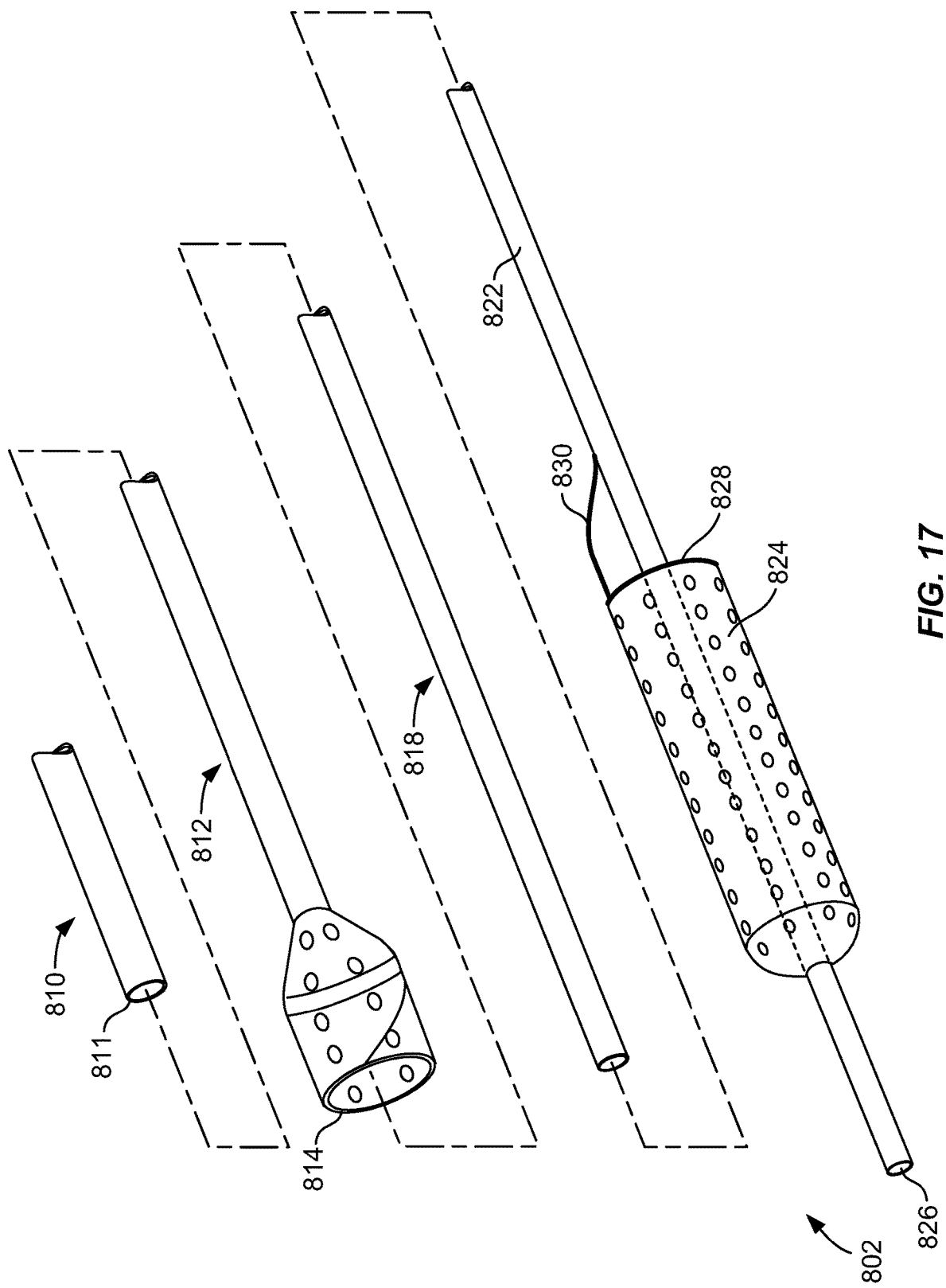
FIG. 17 is an exploded view of a shaft assembly of the eighth clot retrieval device embodiment of FIG. 16.

Referring now to FIGS. 16 and 17, an eighth embodiment of a clot retriever 800 constructed in accordance with the principles of the present invention will be described. The clot retriever system 800 comprises a shaft assembly 802 and a handle assembly 804. A clot retrieval assembly 806 is at the distal end of the shaft assembly 802, and the handle assembly 804 is attached at a proximal end to the shaft assembly.

With particular reference to FIG. 17, the shaft assembly 802 comprises an outer sheath 810 which is fixedly attached at its proximal end to the handle assembly 804. A funnel sheath 812 having a self-expanding funnel 814 is slideably received within a lumen of the outer sheath 810. A net delivery sheath 818 is similarly slideably received in a lumen of the funnel sheath 812, and finally a net deployment sheath shaft 822 is slideably received within a lumen of the net delivery sheath 818. A radially expandable net structure 824 is attached near a distal end of the net deployment shaft and has a closed end on its distal side and an open end on its proximal side. A radially self-expanding hoop wire 828 is formed around a peripheral edge of the open end of the net 824 in a manner similar to the net structures in the previous embodiments. In addition, the hoop wire 828 is secured to the net deployment shaft 822 by a stabilizing wire 830. A combination of the self-opening hoop wire 828 and the stabilizing wire 830, both of which are typically made of a highly elastic metal, such as nickel-titanium alloy, assures that the net 824 will open as it emerges from the constraint of the net delivery sheath 818 and further that the net will remain fully extended or stretched in the axial direction in order to maximize the volume available for clot capture. The net deployment shaft 822 will typically have a lumen, such as a guidewire lumen 826 so that the clot retrievers may be introduced to the vasculature over a guidewire in a conventional manner.

As illustrated in FIGS. 16 and 17, both the funnel 814 and the net 824 are shown as perforated membranes or sheets, typically being pre-shaped in an open-ended cup-like configuration. It will be appreciated that other net configurations as described previously could also be employed, including mesh structures, permeable fabric structures, stent-like scaffolds, scaffold-supported graft-like structures, and the like.

Figure 18A:
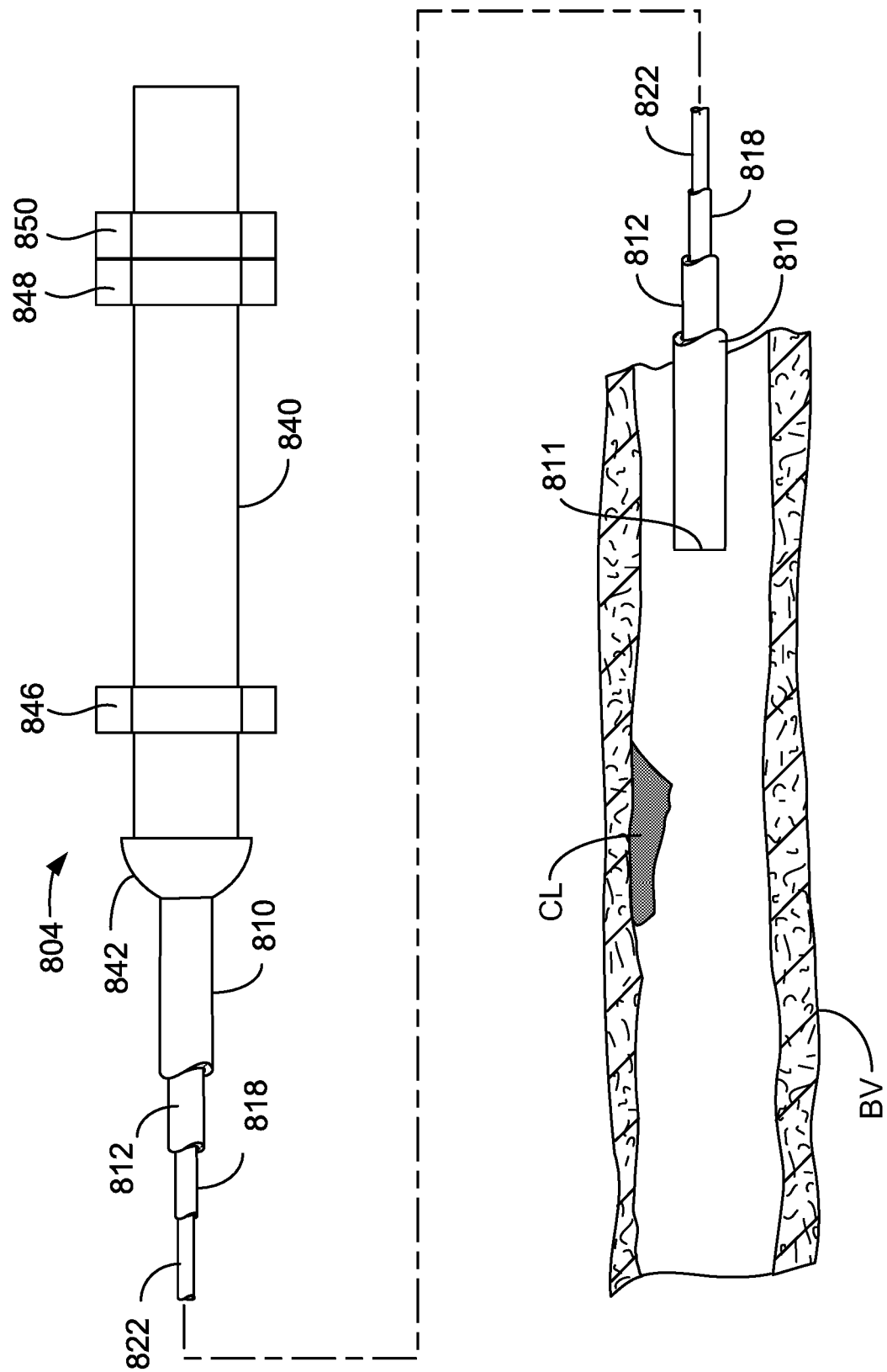
FIGS. 18A through 18F use of the eighth clot retrieval device of FIGS. 16 and 17 in removing clot from a blood vessel in accordance with the principles of the present invention.
Figure 18B:
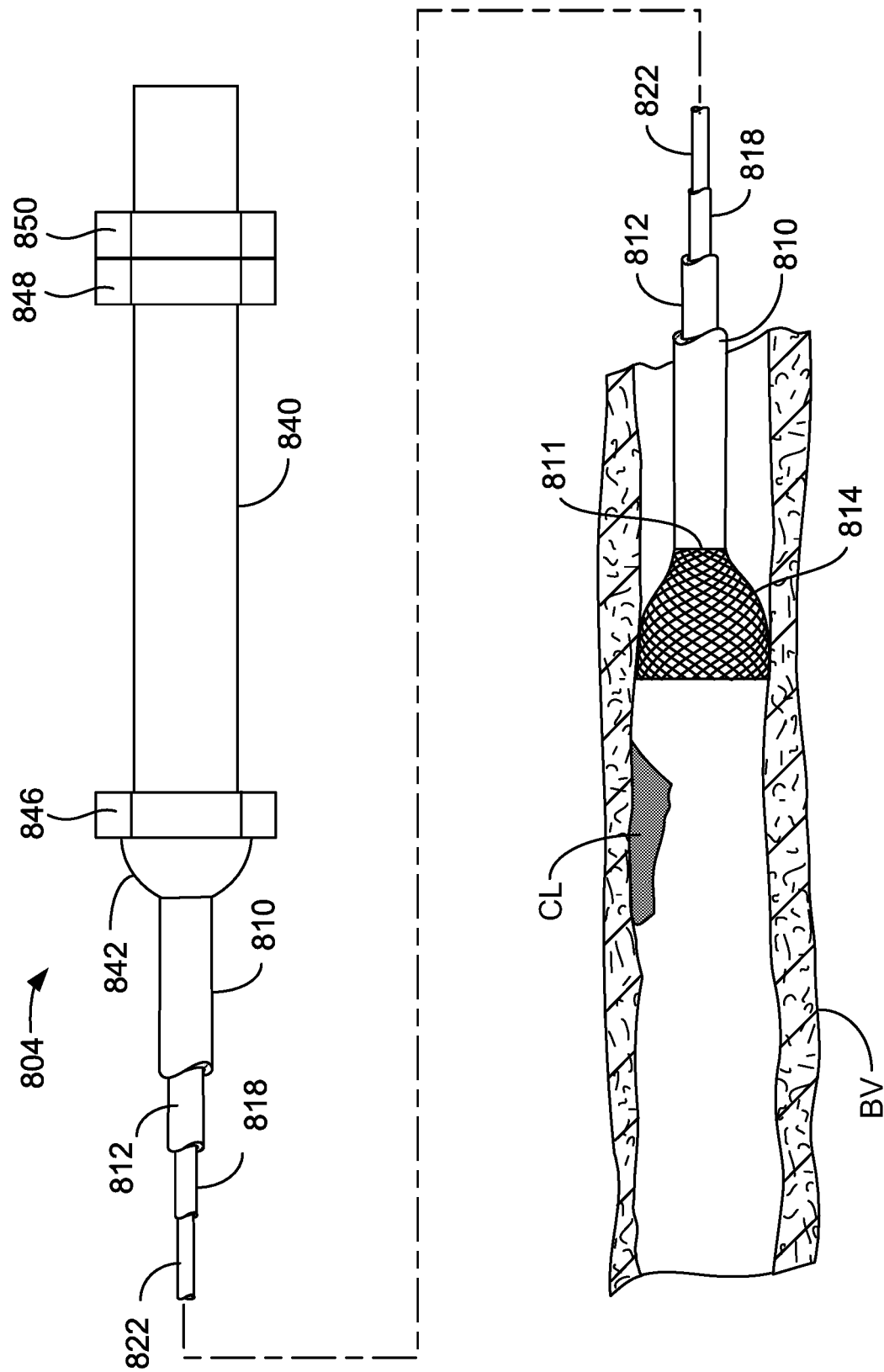

Referring now to FIGS. 18A through 18F, use of the clot retrieval system 800 for removing clot CL from a blood vessel BV will be described. Initially, as shown in FIG. 18A, a distal end 811 of the outer sheath 810 of the clot retriever is advanced in a lumen of the blood vessel BV to a location on one side of the clot CL. Typically, the clot retriever will be introduced over a guidewire, but illustration of the guidewire is omitted for simplification.

After the distal end 811 of the outer sheath 810 is properly positioned, a user can deploy the funnel 814 by manually advancing a funnel deployment slide 846 which is on is slidably disposed on an exterior of a cylindrical body 840 of the handle assembly 804. The funnel deployment slide 846 will typically be advanced until it reaches an enlarged distal nose component at the distal end of the body 840 of the handle 804, at which point the funnel 814 will be fully deployed as shown in FIG. 16.

Figure 18C:
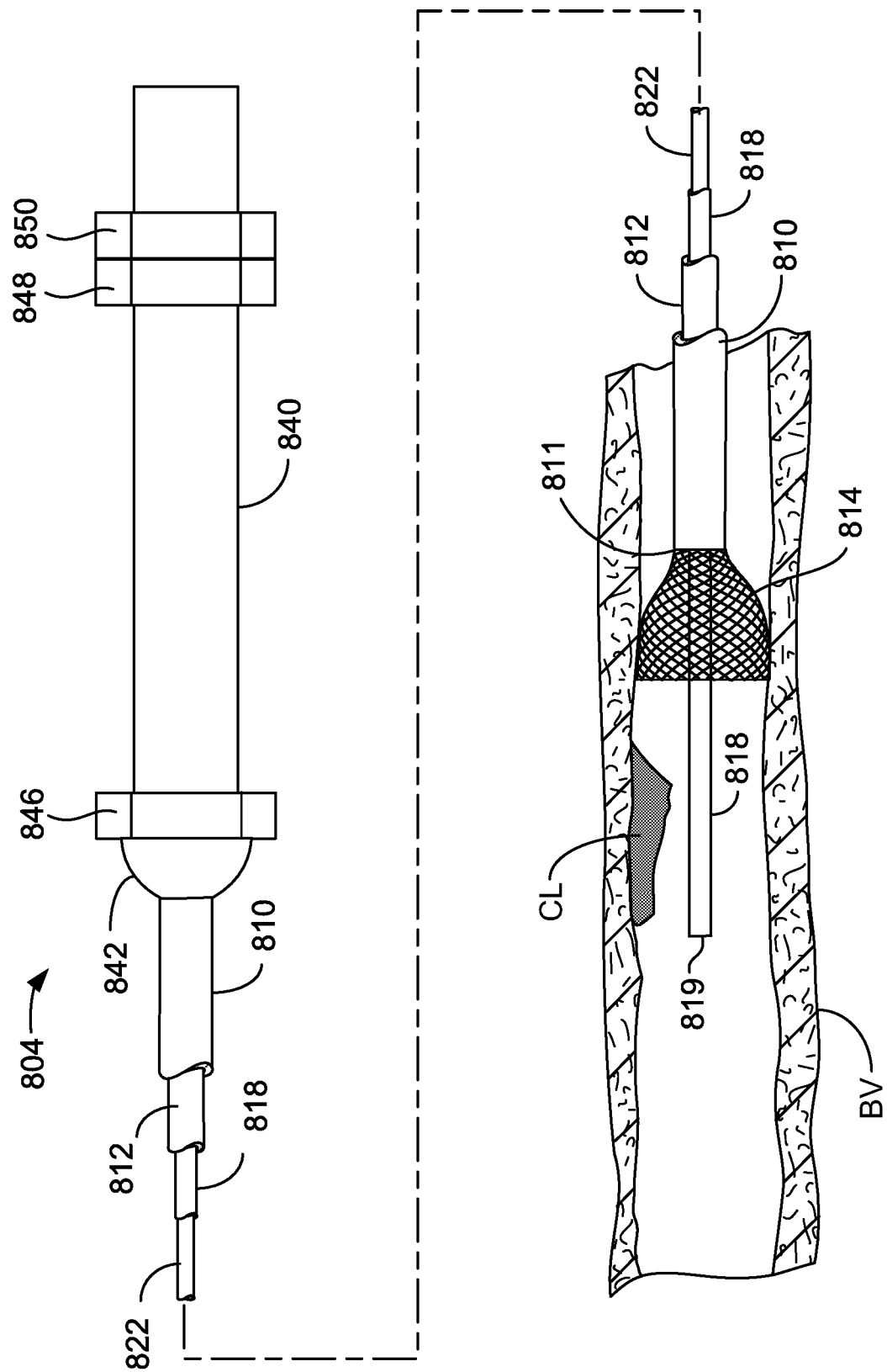

After the funnel 814 has been deployed, the net deployment sheath 818 may be distally advanced by moving a net sheath slide 848 and net advancement slide 850 in tandem in a distal direction on the handle, shown in FIG. 18C. The slides 848 and 850 will be moved sufficiently in a distal direction to advance a distal end 819 of the net delivery sheath 818 distally beyond the region of clot CL.

Figure 18D:
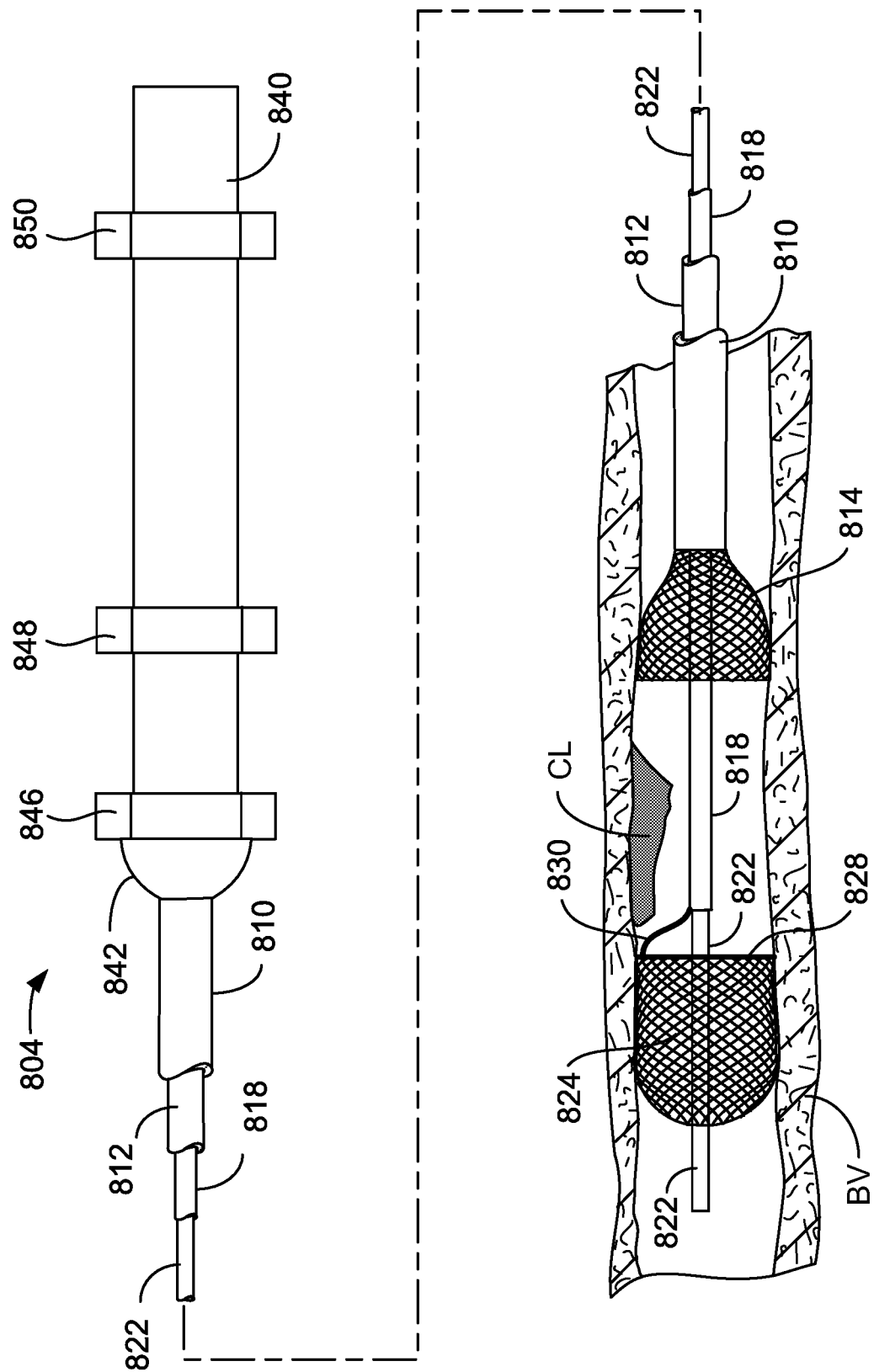

Once the distal end 819 of the net delivery sheath 818 has been advanced beyond the region of clot CL, the net deployment shaft 822 may be advanced from the net deployment sheath 818 by distally advancing the net advancement slide 848 while leaving the net sheath slide 850 in place as shown in FIG. 18D. Once released from the constraint of the net delivery sheath 818, the net 824 will radially expand and axially elongate so that it is prepared to be proximally retracted into the funnel 814 in order to capture the clot CL therebetween.

Figure 18E:
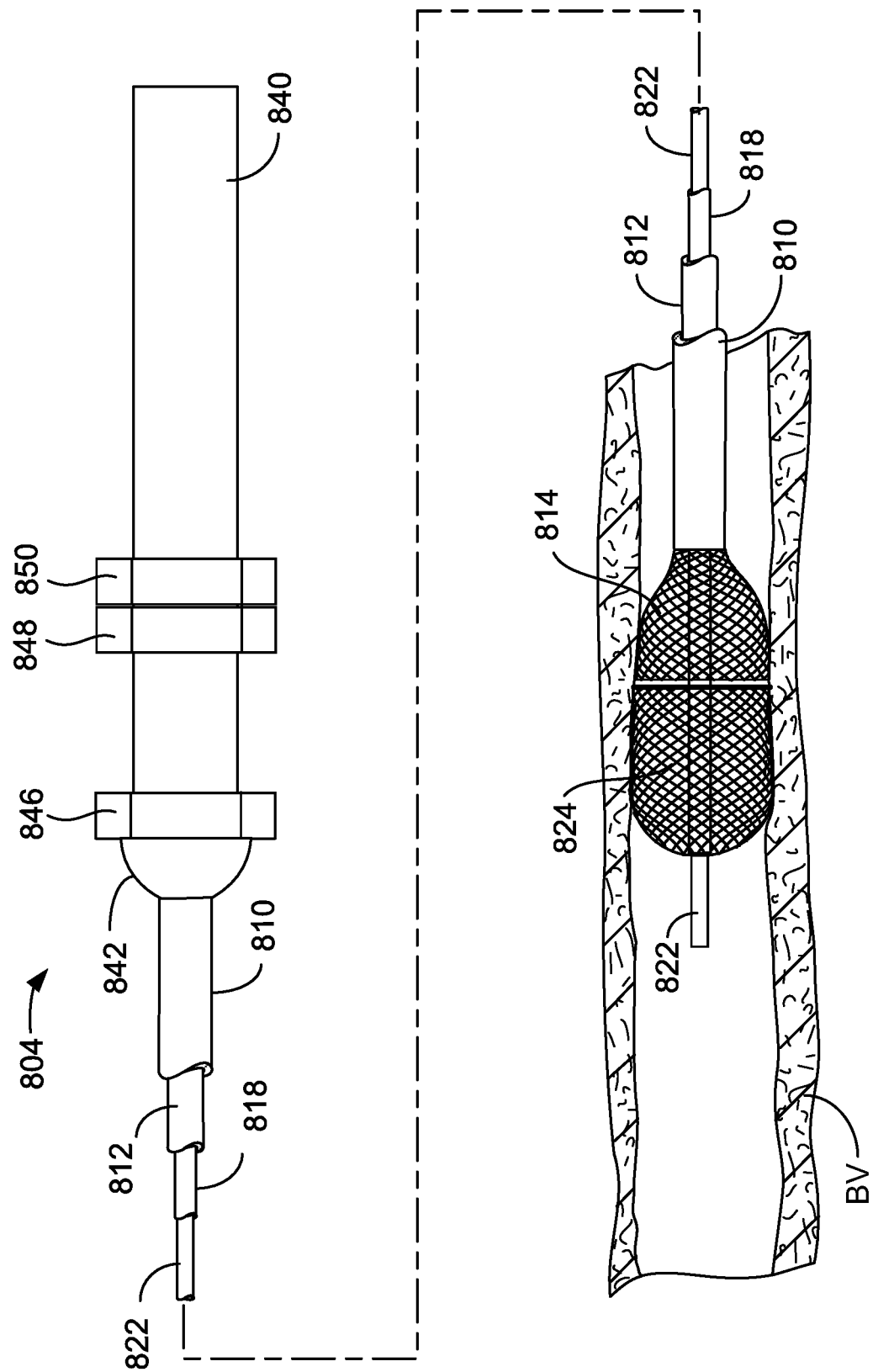

As shown in FIG. 18E, the net advancement slide 850 may be proximally retracted back to the net sheath 848, causing the net 824 to close against the funnel 814. Typically, the net 824 will continue to be proximally retracted so that it is drawn to within an interior of the funnel 814.

Once the clot is fully captured between the net 824 and the funnel 814, the combination of the net and funnel may then be retracted back within the central lumen of the outer sheath 810, shown in FIG. 18E. In particular, each of the slides 846, 848, and 850 will be proximally retracted on the handle to draw the net 824 and the funnel 814 back into the outer sheath in tandem with minimum risk of losing the captured clot.

During advancement and retraction of the slides 846, 848, and 850, the latches 854 and 858 may be used to maintain a fixed spacing between the slides as well as the net 824, funnel 814, and the net deployment shaft 822.

Figure 18F:
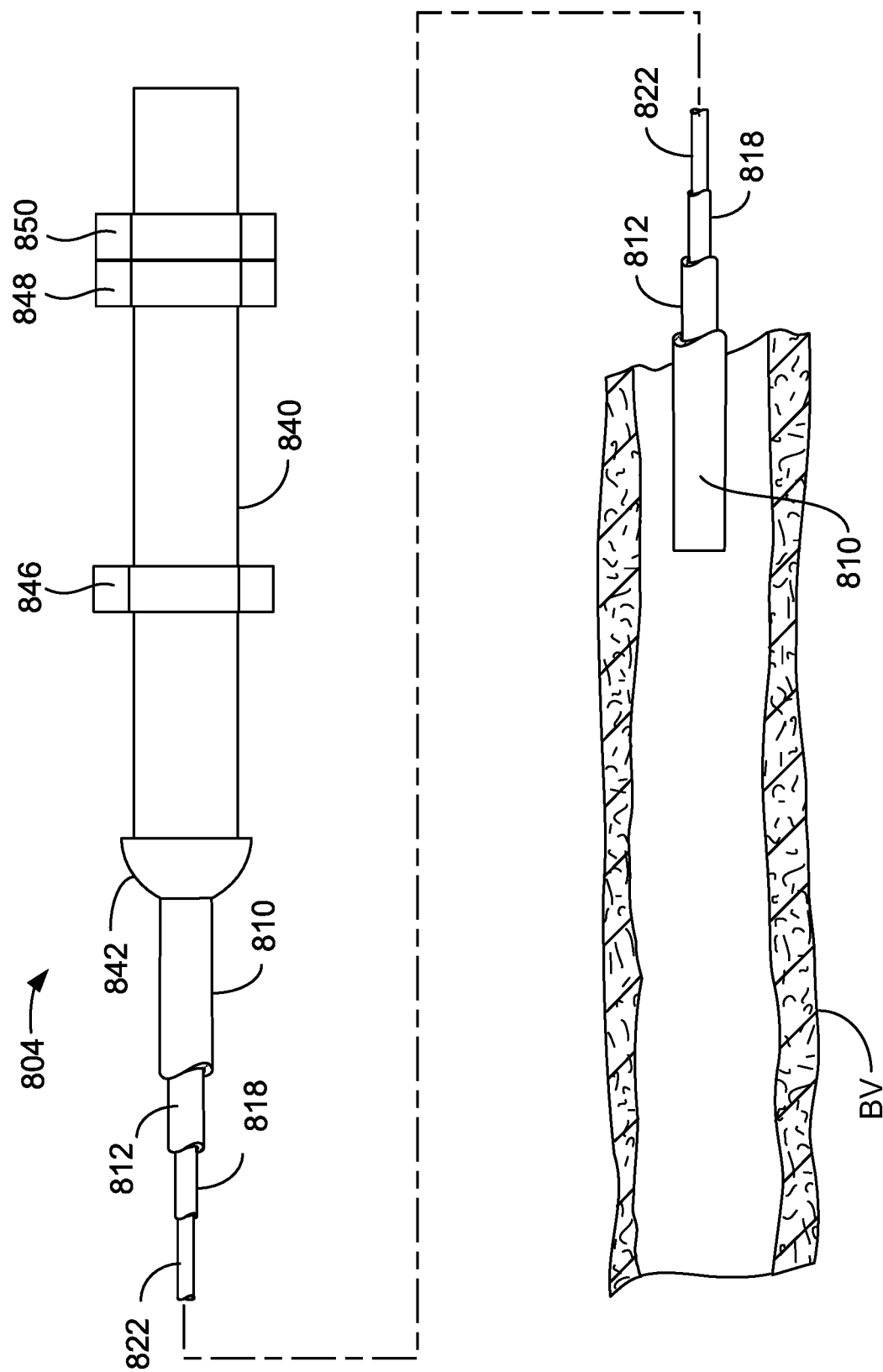

After the clot CL is captured between the net 824 and the funnel 814, as shown in FIG. 18E, the clot may be too large to capture and retrieve as shown in FIG. 18F. In such cases, the entire assembly of the net 824 and the funnel 814 maybe retracted as a capsule-like structure with clot inside and without having been retracted into the outer sheath 810.

While the preferred embodiments of the devices and methods have been described in reference to the environment in which they were developed, they are merely illustrative of the principles of the present inventive concepts. Modification or combinations of the above-described assemblies, other embodiments, configurations, and methods for carrying out the invention, and variations of aspects of the invention that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth herebelow not be construed as being order-specific unless such order specificity is expressly stated in the claim.

What is claimed is:

1. A method for retrieving clot from a blood vessel, said method comprising;
   advancing a net delivery sheath in a distal direction through a blood vessel and past a region of clot;
   advancing a net shaft in the distal direction from a distal end of the net delivery sheath, wherein
   advancing the net shaft in the distal direction deploys (a) a collapsible hoop coupled to a distal end of the net shaft laterally relative to a longitudinal axis of the net shaft and (b) a funnel attached to the distal end of the net shaft proximally of the collapsible hoop as the collapsible hoop emerges from the net delivery sheath; and
   drawing the net shaft in a proximal direction to pass the funnel over and past the region of clot wherein the funnel moves in tandem with the collapsible hoop and funnels clot from the region of clot into a clot collection net carried by the collapsible hoop as the net shaft is drawn in the proximal direction, wherein the funnel and the collapsible hoop remain in axially fixed positions relative to each other as they are drawn in the proximal direction.

2. A method as in claim 1, further comprising advancing a main delivery tube in the distal direction through the blood vessel, wherein the main delivery tube carries the net delivery sheath as the main delivery tube is advanced.

3. A method as in claim 2, wherein the main delivery tube further carries a net delivery tube which carries the clot collection net, wherein the net shaft is drawn proximally to pull the clot collection net from the net delivery tube.

4. A method as in claim 1, wherein the blood vessel is a coronary artery.

5. A method as in claim 1, wherein the blood vessel is a Superior Vena Cava, an Inferior Vena Cava or a peripheral vein.

6. A method as in claim 1, wherein the blood vessel is an aorta, a carotid artery or a peripheral artery.

* * * * *